US012040096B2

United States Patent
Booth et al.

(10) Patent No.: US 12,040,096 B2
(45) Date of Patent: Jul. 16, 2024

(54) DIABETES MANAGEMENT THERAPY ADVISOR

(71) Applicant: Aseko, Inc., Greenville, SC (US)

(72) Inventors: Robert C. Booth, Greer, SC (US); Harry Hebblewhite, Atlanta, GA (US)

(73) Assignee: Aseko, Inc., Greenville, SC (US)

( * ) Notice: Subject to any disclaimer, the term of this patent is extended or adjusted under 35 U.S.C. 154(b) by 0 days.

(21) Appl. No.: 18/165,306

(22) Filed: Feb. 6, 2023

(65) Prior Publication Data

US 2023/0187083 A1    Jun. 15, 2023

Related U.S. Application Data

(63) Continuation of application No. 17/454,054, filed on Nov. 8, 2021, now Pat. No. 11,574,742, which is a
(Continued)

(51) Int. Cl.
*G16H 70/20*    (2018.01)
*G16H 10/60*    (2018.01)
(Continued)

(52) U.S. Cl.
CPC ............. *G16H 70/20* (2018.01); *G16H 10/60* (2018.01); *G16H 20/10* (2018.01); *G16H 20/17* (2018.01); *G16H 50/00* (2018.01); *G16H 50/20* (2018.01)

(58) Field of Classification Search
CPC ........ G16H 70/20; G16H 10/60; G16H 20/10; G16H 20/17; G16H 50/00; G16H 50/20;
(Continued)

(56) References Cited

U.S. PATENT DOCUMENTS

| 561,422 A | 6/1896 | Minnis |
| 4,055,175 A | 10/1977 | Clemens et al. |

(Continued)

FOREIGN PATENT DOCUMENTS

| AU | 199460325 A | 8/1994 |
| AU | 2009283013 A1 | 2/2010 |

(Continued)

OTHER PUBLICATIONS

Kim, Sarah et al., Hyperglycemia control of the Nil per os patient in the intensive care unit: Introduction of a simple subcutaneous insulin algorithm, Journal of Diabetes Science and Technology, Nov. 2012, vol. 6, Issue 6, pp. 1413-1419.
(Continued)

*Primary Examiner* — Robert A Sorey
*Assistant Examiner* — Kimberly A. Sass
(74) *Attorney, Agent, or Firm* — Honigman LLP; Brett A. Krueger; Grant Griffith

(57) ABSTRACT

A method includes obtaining training data for a plurality of patients of a patient population. The training data includes training blood glucose history data including treatment doses of insulin administered by the patients of the patient population and one or more outcome attributes associated with each treatment dose. The method also includes identifying, for each patient of the patient population, one or more optimum treatment doses of insulin from the treatment doses yielding favorable outcome attributes. The method also includes receiving patient-state information for the treated patient, determining a next recommended treatment dose of insulin for the treated patient based on one or more of the identified optimum treatment doses associated with the patients of the patient population having training patient-state information similar to the patient-state information for the treated patient, and transmitting the next recommended
(Continued)

treatment dose to a portable device associated with the treated patient.

24 Claims, 14 Drawing Sheets

Related U.S. Application Data continuation of application No. 16/503,048, filed on Jul. 3, 2019, now Pat. No. 11,200,988, which is a continuation of application No. 15/851,733, filed on Dec. 21, 2017, now Pat. No. 10,380,328, which is a continuation of application No. 15/241,703, filed on Aug. 19, 2016, now Pat. No. 9,886,556.

(60) Provisional application No. 62/207,613, filed on Aug. 20, 2015.

(51) Int. Cl.
*G16H 20/10* (2018.01)
*G16H 20/17* (2018.01)
*G16H 50/00* (2018.01)
*G16H 50/20* (2018.01)

(58) Field of Classification Search
CPC .... G16H 20/60; G16H 40/67; A61B 5/14532; A61B 5/746; A61B 5/145
See application file for complete search history.

(56) References Cited

U.S. PATENT DOCUMENTS

| | | | |
|---|---|---|---|
| 4,151,845 A | 5/1979 | Clemens |
| 4,206,755 A | 6/1980 | Klein |
| 4,403,984 A | 9/1983 | Ash et al. |
| 4,464,170 A | 8/1984 | Clemens et al. |
| 4,731,726 A | 3/1988 | Allen, III |
| 4,850,959 A | 7/1989 | Findl |
| 4,911,168 A | 3/1990 | Davis |
| 4,947,845 A | 8/1990 | Davis |
| 4,981,779 A | 1/1991 | Wagner |
| 5,091,190 A | 2/1992 | Kuczynski et al. |
| 5,216,597 A | 6/1993 | Beckers |
| 5,251,126 A | 10/1993 | Kahn et al. |
| 5,822,715 A | 10/1998 | Worthington et al. |
| 5,956,501 A | 9/1999 | Brown |
| 5,998,363 A | 12/1999 | Forse et al. |
| 6,024,699 A | 2/2000 | Surwit et al. |
| 6,186,145 B1 | 2/2001 | Brown |
| 6,233,539 B1 | 5/2001 | Brown |
| 6,379,301 B1 | 4/2002 | Worthington et al. |
| 6,428,825 B2 | 8/2002 | Sharma et al. |
| 6,472,366 B2 | 10/2002 | Kishino et al. |
| 6,540,672 B1 | 4/2003 | Simonsen et al. |
| 6,544,212 B2 | 4/2003 | Galley et al. |
| 6,560,471 B1 | 5/2003 | Heller et al. |
| 6,572,542 B1 | 6/2003 | Houben et al. |
| 6,575,905 B2 | 6/2003 | Knobbe et al. |
| 6,605,039 B2 | 8/2003 | Houben et al. |
| 6,615,081 B1 | 9/2003 | Boveja |
| 6,669,663 B1 | 12/2003 | Thompson |
| 6,740,072 B2 | 5/2004 | Starkweather et al. |
| 6,808,703 B2 | 10/2004 | Park et al. |
| 6,890,568 B2 | 5/2005 | Pierce et al. |
| 6,927,246 B2 | 8/2005 | Noronha et al. |
| 7,025,425 B2 | 4/2006 | Kovatchev et al. |
| 7,039,560 B2 | 5/2006 | Kawatahara et al. |
| 7,060,059 B2 | 6/2006 | Keith et al. |
| 7,108,680 B2 | 9/2006 | Rohr et al. |
| 7,137,951 B2 | 11/2006 | Pilarski |
| 7,167,818 B2 | 1/2007 | Brown |
| 7,204,823 B2 | 4/2007 | Estes et al. |
| 7,267,665 B2 | 9/2007 | Steil et al. |
| 7,282,029 B1 | 10/2007 | Poulsen et al. |
| 7,291,107 B2 | 11/2007 | Hellwig et al. |
| 7,404,796 B2 | 7/2008 | Ginsberg |
| 7,498,318 B1 | 3/2009 | Stahl et al. |
| 7,509,156 B2 | 3/2009 | Flanders |
| 7,553,281 B2 | 6/2009 | Hellwig et al. |
| 7,651,845 B2 | 1/2010 | Doyle, III et al. |
| 7,704,226 B2 | 4/2010 | Mueller, Jr. et al. |
| 7,734,323 B2 | 6/2010 | Blomquist et al. |
| 7,806,886 B2 | 10/2010 | Kanderian, Jr. et al. |
| 7,824,333 B2 | 11/2010 | Otto et al. |
| 7,837,622 B2 | 11/2010 | Itoh et al. |
| 7,853,455 B2 | 12/2010 | Brown |
| 7,877,271 B2 | 1/2011 | Brown |
| 7,901,625 B2 | 3/2011 | Brown |
| 7,904,310 B2 | 3/2011 | Brown |
| 7,912,688 B2 | 3/2011 | Brown |
| 7,920,998 B2 | 4/2011 | Brown |
| 7,949,507 B2 | 5/2011 | Brown |
| 7,985,848 B2 | 7/2011 | Woo et al. |
| 8,088,731 B2 | 1/2012 | Knudsen et al. |
| 8,117,020 B2 | 2/2012 | Abensour et al. |
| 8,185,412 B1 | 5/2012 | Harpale |
| 8,198,320 B2 | 6/2012 | Liang et al. |
| 8,204,729 B2 | 6/2012 | Sher |
| 8,206,340 B2 | 6/2012 | Arefieg |
| 8,257,300 B2 | 9/2012 | Budiman et al. |
| 8,257,735 B2 | 9/2012 | Lau et al. |
| 8,318,221 B2 | 11/2012 | Miller et al. |
| 8,329,232 B2 | 12/2012 | Cheng et al. |
| 8,333,752 B2 | 12/2012 | Veit et al. |
| 8,370,077 B2 | 2/2013 | Bashan et al. |
| 8,398,616 B2 | 3/2013 | Budiman |
| 8,420,125 B2 | 4/2013 | Webster et al. |
| 8,420,621 B2 | 4/2013 | Lai et al. |
| 8,457,901 B2 | 6/2013 | Beshan et al. |
| 8,527,208 B2 | 9/2013 | Prud'homme et al. |
| 8,532,933 B2 | 9/2013 | Duke et al. |
| 8,548,544 B2 | 10/2013 | Kircher, Jr. et al. |
| 8,571,801 B2 | 10/2013 | Anfinsen et al. |
| 8,579,879 B2 | 11/2013 | Palerm et al. |
| 8,600,682 B2 | 12/2013 | Bashan et al. |
| 8,635,054 B2 | 1/2014 | Brown |
| 8,679,016 B2 | 3/2014 | Mastrototaro et al. |
| 8,690,934 B2 | 4/2014 | Boyden et al. |
| 8,700,161 B2 | 4/2014 | Harel et al. |
| 8,703,183 B2 | 4/2014 | Lara |
| 8,718,949 B2 | 5/2014 | Blomquist et al. |
| 8,755,938 B2 | 6/2014 | Weinert et al. |
| 8,766,803 B2 | 7/2014 | Bousamra et al. |
| 8,828,390 B2 | 9/2014 | Herrera et al. |
| 8,834,367 B2 | 9/2014 | Laan et al. |
| 8,870,807 B2 | 10/2014 | Mantri et al. |
| 8,911,367 B2 | 12/2014 | Brister et al. |
| 8,919,180 B2 | 12/2014 | Gottlieb et al. |
| 8,992,464 B2 | 3/2015 | Bashan et al. |
| 2001/0002269 A1 | 5/2001 | Zhao |
| 2003/0028089 A1 | 2/2003 | Galley et al. |
| 2003/0050621 A1 | 3/2003 | Lebel et al. |
| 2003/0199445 A1 | 10/2003 | Knudsen et al. |
| 2003/0208110 A1 | 11/2003 | Mault et al. |
| 2004/0042272 A1 | 3/2004 | Kurata |
| 2004/0044272 A1 | 3/2004 | Moerman et al. |
| 2004/0054263 A1 | 3/2004 | Moerman et al. |
| 2005/0020681 A1 | 1/2005 | Takayama et al. |
| 2005/0049179 A1 | 3/2005 | Davidson et al. |
| 2005/0054818 A1 | 3/2005 | Brader et al. |
| 2005/0055010 A1 | 3/2005 | Pettis et al. |
| 2005/0096637 A1 | 5/2005 | Heruth |
| 2005/0171503 A1 | 8/2005 | Van Den Berghe et al. |
| 2005/0176621 A1 | 8/2005 | Brader et al. |
| 2005/0177398 A1 | 8/2005 | Watanabe et al. |
| 2005/0187749 A1 | 8/2005 | Singley |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0267195 A1 | 12/2005 | Mikoshiba et al. |
| 2005/0272640 A1 | 12/2005 | Doyle et al. |
| 2006/0040003 A1 | 2/2006 | Needleman et al. |

(56) References Cited

U.S. PATENT DOCUMENTS

| | | |
|---|---|---|
| 2006/0078593 A1 | 4/2006 | Strozier et al. |
| 2006/0160722 A1 | 7/2006 | Green et al. |
| 2006/0173260 A1 | 8/2006 | Gaoni et al. |
| 2006/0188995 A1 | 8/2006 | Ryan et al. |
| 2006/0224109 A1 | 10/2006 | Steil et al. |
| 2006/0264895 A1 | 11/2006 | Flanders |
| 2007/0036872 A1 | 2/2007 | Tsuboi et al. |
| 2007/0060796 A1 | 3/2007 | Kim |
| 2007/0078314 A1 | 4/2007 | Grounsell et al. |
| 2007/0078818 A1 | 4/2007 | Zivitz et al. |
| 2007/0160678 A1 | 7/2007 | Guimberteau et al. |
| 2007/0168224 A1 | 7/2007 | Letzt et al. |
| 2007/0179434 A1 | 8/2007 | Weinert et al. |
| 2007/0249916 A1 | 10/2007 | Pesach et al. |
| 2007/0282186 A1 | 12/2007 | Gilmore |
| 2007/0293742 A1 | 12/2007 | Simonsen et al. |
| 2008/0097289 A1 | 4/2008 | Steil et al. |
| 2008/0119421 A1 | 5/2008 | Tuszynski et al. |
| 2008/0119705 A1 | 5/2008 | Patel et al. |
| 2008/0139511 A1 | 6/2008 | Friesen |
| 2008/0139907 A1 | 6/2008 | Rao et al. |
| 2008/0172030 A1 | 7/2008 | Blomquist |
| 2008/0188796 A1 | 8/2008 | Steil et al. |
| 2008/0214919 A1 | 9/2008 | Harmon et al. |
| 2008/0228056 A1 | 9/2008 | Blomquist et al. |
| 2008/0234943 A1 | 9/2008 | Ray et al. |
| 2008/0255707 A1 | 10/2008 | Hebblewhite et al. |
| 2008/0269585 A1 | 10/2008 | Ginsberg |
| 2008/0299079 A1 | 12/2008 | Meezan et al. |
| 2008/0306353 A1 | 12/2008 | Douglas et al. |
| 2009/0006061 A1 | 1/2009 | Thukral et al. |
| 2009/0029933 A1 | 1/2009 | Velloso et al. |
| 2009/0036753 A1 | 2/2009 | King |
| 2009/0054753 A1 | 2/2009 | Robinson et al. |
| 2009/0069636 A1 | 3/2009 | Zivitz et al. |
| 2009/0099438 A1 | 4/2009 | Flanders |
| 2009/0110752 A1 | 4/2009 | Shang et al. |
| 2009/0157430 A1 | 6/2009 | Rule et al. |
| 2009/0214511 A1 | 8/2009 | Tran et al. |
| 2009/0227514 A1 | 9/2009 | Oben |
| 2009/0239944 A1 | 9/2009 | D'orazio et al. |
| 2009/0240127 A1 | 9/2009 | Ray |
| 2009/0242399 A1 | 10/2009 | Kamath et al. |
| 2009/0247982 A1 | 10/2009 | Krulevitch et al. |
| 2009/0253970 A1 | 10/2009 | Bashan et al. |
| 2009/0253973 A1 | 10/2009 | Bashan et al. |
| 2009/0281519 A1 | 11/2009 | Rao et al. |
| 2009/0299152 A1 | 12/2009 | Taub et al. |
| 2009/0312250 A1 | 12/2009 | Ryu et al. |
| 2010/0016700 A1 | 1/2010 | Sieh et al. |
| 2010/0035795 A1 | 2/2010 | Boss et al. |
| 2010/0137788 A1 | 6/2010 | Braithwaite et al. |
| 2010/0145725 A1 | 6/2010 | Alferness et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0168660 A1 | 7/2010 | Galley et al. |
| 2010/0198142 A1 | 8/2010 | Sloan et al. |
| 2010/0256047 A1 | 10/2010 | Sieh et al. |
| 2010/0262434 A1 | 10/2010 | Shaya |
| 2010/0286601 A1 | 11/2010 | Yodfat et al. |
| 2010/0305545 A1 | 12/2010 | Kanderian, Jr. et al. |
| 2010/0324382 A1 | 12/2010 | Cantwell et al. |
| 2010/0331652 A1 | 12/2010 | Groll et al. |
| 2010/0331654 A1 | 12/2010 | Jerdonek et al. |
| 2010/0332142 A1 | 12/2010 | Shadforth et al. |
| 2011/0021894 A1 | 1/2011 | Mohanty et al. |
| 2011/0071365 A1 | 3/2011 | Lee et al. |
| 2011/0071464 A1 | 3/2011 | Palerm |
| 2011/0098548 A1 | 4/2011 | Budiman et al. |
| 2011/0115894 A1 | 5/2011 | Burnett |
| 2011/0119081 A1 | 5/2011 | Vespasiani |
| 2011/0152830 A1 | 6/2011 | Ruchti et al. |
| 2011/0178008 A1 | 7/2011 | Arai et al. |
| 2011/0202486 A1* | 8/2011 | Fung .................... G16H 50/70 |
| | | 706/46 |
| 2011/0213332 A1 | 9/2011 | Mozayeny |
| 2011/0217396 A1 | 9/2011 | Oldani |
| 2011/0218489 A1 | 9/2011 | Mastrototaro et al. |
| 2011/0229602 A1 | 9/2011 | Aymard et al. |
| 2011/0286984 A1 | 11/2011 | Huang |
| 2011/0305771 A1 | 12/2011 | Sampalis |
| 2011/0313674 A1 | 12/2011 | Duke et al. |
| 2011/0319322 A1 | 12/2011 | Bashan et al. |
| 2012/0003339 A1 | 1/2012 | Minacapelli |
| 2012/0022353 A1 | 1/2012 | Bashan et al. |
| 2012/0041778 A1* | 2/2012 | Kraft ................... B65D 51/2828 |
| | | 215/250 |
| 2012/0046606 A1 | 2/2012 | Arefieg |
| 2012/0053222 A1 | 3/2012 | Gorrell et al. |
| 2012/0058942 A1 | 3/2012 | Dupre |
| 2012/0065482 A1 | 3/2012 | Robinson et al. |
| 2012/0095311 A1 | 4/2012 | Ramey et al. |
| 2012/0123234 A1 | 5/2012 | Atlas et al. |
| 2012/0197358 A1 | 8/2012 | Prescott |
| 2012/0213886 A1 | 8/2012 | Gannon et al. |
| 2012/0227737 A1 | 9/2012 | Mastrototaro et al. |
| 2012/0232519 A1 | 9/2012 | Georgiou et al. |
| 2012/0232520 A1 | 9/2012 | Sloan et al. |
| 2012/0238853 A1 | 9/2012 | Arefieg |
| 2012/0244096 A1 | 9/2012 | Xie et al. |
| 2012/0295985 A1 | 11/2012 | Miller et al. |
| 2013/0022592 A1 | 1/2013 | Vaughn et al. |
| 2013/0030358 A1 | 1/2013 | Yodfat et al. |
| 2013/0052285 A1 | 2/2013 | Song et al. |
| 2013/0109620 A1 | 5/2013 | Riis et al. |
| 2013/0144283 A1 | 6/2013 | Barman |
| 2013/0158503 A1 | 6/2013 | Kanderian, Jr. et al. |
| 2013/0165901 A1 | 6/2013 | Ruchti et al. |
| 2013/0190583 A1 | 7/2013 | Grosman et al. |
| 2013/0225683 A1 | 8/2013 | Gagnon et al. |
| 2013/0233727 A1 | 9/2013 | Tsai et al. |
| 2013/0245547 A1 | 9/2013 | El-Khatib et al. |
| 2013/0267796 A1 | 10/2013 | Enric Monte Moreno |
| 2013/0281796 A1 | 10/2013 | Pan |
| 2013/0282301 A1 | 10/2013 | Rush |
| 2013/0289883 A1 | 10/2013 | Bashan et al. |
| 2013/0309750 A1 | 11/2013 | Tajima et al. |
| 2013/0316029 A1 | 11/2013 | Pan et al. |
| 2013/0317316 A1 | 11/2013 | Kandeel |
| 2013/0331323 A1 | 12/2013 | Wu et al. |
| 2013/0338209 A1 | 12/2013 | Gambhire et al. |
| 2013/0345664 A1 | 12/2013 | Beck et al. |
| 2014/0000338 A1 | 1/2014 | Luo et al. |
| 2014/0004211 A1 | 1/2014 | Choi et al. |
| 2014/0024907 A1 | 1/2014 | Howell et al. |
| 2014/0032196 A1* | 1/2014 | Albisser ................. G16H 15/00 |
| | | 703/11 |
| 2014/0037749 A1 | 2/2014 | Shea et al. |
| 2014/0057331 A1 | 2/2014 | Tajima et al. |
| 2014/0066735 A1 | 3/2014 | Engelhardt et al. |
| 2014/0066888 A1 | 3/2014 | Parikh et al. |
| 2014/0081196 A1 | 3/2014 | Chen |
| 2014/0128706 A1 | 5/2014 | Roy |
| 2014/0170123 A1 | 6/2014 | Alam et al. |
| 2014/0178509 A1 | 6/2014 | Jia |
| 2014/0179629 A1 | 6/2014 | Hamaker et al. |
| 2014/0194788 A1 | 7/2014 | Muehlbauer et al. |
| 2014/0213963 A1 | 7/2014 | Wu et al. |
| 2014/0296943 A1 | 10/2014 | Maxik et al. |
| 2014/0303466 A1 | 10/2014 | Fitzpatrick et al. |
| 2014/0303552 A1 | 10/2014 | Kanderian, Jr. et al. |
| 2014/0337041 A1 | 11/2014 | Madden et al. |
| 2014/0347491 A1 | 11/2014 | Connor |
| 2014/0349256 A1 | 11/2014 | Connor |
| 2014/0349257 A1 | 11/2014 | Connor |
| 2014/0356420 A1 | 12/2014 | Huang |
| 2014/0363794 A1 | 12/2014 | Angelides |
| 2014/0365534 A1 | 12/2014 | Bousamra et al. |
| 2014/0378381 A1 | 12/2014 | Chen et al. |
| 2014/0378793 A1 | 12/2014 | Kamath et al. |
| 2015/0018633 A1 | 1/2015 | Kovachev et al. |
| 2015/0025496 A1 | 1/2015 | Imran |

(56) References Cited

U.S. PATENT DOCUMENTS

| | | | |
|---|---|---|---|
| 2015/0025903 A1 | 1/2015 | Mueller-Wolf | |
| 2015/0031053 A1 | 1/2015 | Moerman | |
| 2015/0037406 A1 | 2/2015 | Martinez et al. | |
| 2015/0217054 A1 | 8/2015 | Booth et al. | |
| 2017/0165425 A9* | 6/2017 | Ruchti | A61B 5/14532 |

FOREIGN PATENT DOCUMENTS

| | | |
|---|---|---|
| AU | 2010330746 A1 | 7/2012 |
| CA | 2519249 A1 | 10/2004 |
| CA | 2670512 A1 | 7/2008 |
| CA | 2720302 A1 | 12/2009 |
| CA | 2720304 A1 | 12/2009 |
| CA | 2733593 A1 | 2/2010 |
| CA | 2752637 A1 | 9/2010 |
| CA | 2761647 A1 | 12/2010 |
| CA | 2766944 A1 | 1/2011 |
| CA | 2784143 A1 | 6/2011 |
| CN | 102016855 A | 4/2011 |
| CN | 102016906 A | 4/2011 |
| CN | 102300501 A | 12/2011 |
| CN | 102395310 A | 3/2012 |
| CN | 102481101 A | 5/2012 |
| CN | 102946804 A | 2/2013 |
| DE | 1082412 T1 | 10/2001 |
| EP | 461207 A1 | 12/1991 |
| EP | 483595 A2 | 5/1992 |
| EP | 557350 A1 | 9/1993 |
| EP | 573499 A1 | 12/1993 |
| EP | 768043 A2 | 4/1997 |
| EP | 862648 A1 | 9/1998 |
| EP | 910578 A2 | 4/1999 |
| EP | 925792 A2 | 6/1999 |
| EP | 1017414 A1 | 7/2000 |
| EP | 1030557 A1 | 8/2000 |
| EP | 1051141 A1 | 11/2000 |
| EP | 1067925 A1 | 1/2001 |
| EP | 1082412 A2 | 3/2001 |
| EP | 1115389 A1 | 7/2001 |
| EP | 483595 | 12/2001 |
| EP | 1173482 A1 | 1/2002 |
| EP | 1185321 A1 | 3/2002 |
| EP | 1196445 A1 | 4/2002 |
| EP | 1214596 A1 | 6/2002 |
| EP | 1305018 A1 | 5/2003 |
| EP | 1317190 A2 | 6/2003 |
| EP | 1382363 A1 | 1/2004 |
| EP | 1424074 A1 | 6/2004 |
| EP | 1482919 A1 | 12/2004 |
| EP | 1581095 A2 | 10/2005 |
| EP | 1610758 A2 | 1/2006 |
| EP | 1679009 A1 | 7/2006 |
| EP | 1698898 A2 | 9/2006 |
| EP | 1773860 A1 | 4/2007 |
| EP | 1846002 A1 | 10/2007 |
| EP | 1885392 A2 | 2/2008 |
| EP | 1915171 A2 | 4/2008 |
| EP | 1921981 A2 | 5/2008 |
| EP | 2114491 A1 | 11/2009 |
| EP | 2129277 A2 | 12/2009 |
| EP | 2139393 A2 | 1/2010 |
| EP | 2170430 A2 | 4/2010 |
| EP | 2257218 A2 | 12/2010 |
| EP | 2260423 A2 | 12/2010 |
| EP | 2260462 A2 | 12/2010 |
| EP | 2276405 A1 | 1/2011 |
| EP | 2300046 A2 | 3/2011 |
| EP | 2328608 A2 | 6/2011 |
| EP | 2352456 A1 | 8/2011 |
| EP | 2355669 A2 | 8/2011 |
| EP | 2377465 A1 | 10/2011 |
| EP | 2384750 A1 | 11/2011 |
| EP | 2393419 A1 | 12/2011 |
| EP | 2400882 A1 | 1/2012 |
| EP | 2418972 A1 | 2/2012 |
| EP | 2442719 A2 | 4/2012 |
| EP | 2448432 A1 | 5/2012 |
| EP | 2448468 A1 | 5/2012 |
| EP | 2448469 A2 | 5/2012 |
| EP | 2482712 A1 | 8/2012 |
| EP | 2516671 A1 | 10/2012 |
| EP | 2518655 A2 | 10/2012 |
| EP | 2525863 A1 | 11/2012 |
| EP | 2535831 A1 | 12/2012 |
| EP | 2552313 A2 | 2/2013 |
| EP | 2582297 A1 | 4/2013 |
| EP | 2585133 A1 | 5/2013 |
| EP | 2590559 A2 | 5/2013 |
| EP | 2596448 A1 | 5/2013 |
| EP | 2603133 A1 | 6/2013 |
| EP | 2605819 A1 | 6/2013 |
| EP | 2640373 A1 | 9/2013 |
| EP | 2641084 A1 | 9/2013 |
| EP | 2644088 A1 | 10/2013 |
| EP | 2654777 A2 | 10/2013 |
| EP | 2659407 A1 | 11/2013 |
| EP | 2666369 A1 | 11/2013 |
| EP | 2685895 A1 | 1/2014 |
| EP | 2720713 A2 | 4/2014 |
| EP | 2736404 A1 | 6/2014 |
| EP | 2742447 A2 | 6/2014 |
| EP | 2742449 A2 | 6/2014 |
| EP | 2745225 A2 | 6/2014 |
| EP | 2760335 A1 | 8/2014 |
| EP | 2763722 A2 | 8/2014 |
| EP | 2798548 A1 | 11/2014 |
| EP | 2822647 A1 | 1/2015 |
| JP | 04800928 B2 | 10/2011 |
| KR | 100527154 B1 | 11/2005 |
| KR | 1020090095073 | 9/2009 |
| KR | 2011052664 A | 5/2011 |
| KR | 2012047841 A | 5/2012 |
| RU | 2011109016 A | 9/2012 |
| WO | 1992019260 A1 | 11/1992 |
| WO | 1996009823 A1 | 4/1996 |
| WO | 1999044496 A1 | 9/1999 |
| WO | 1999063101 A2 | 12/1999 |
| WO | 2002036139 | 5/2002 |
| WO | 2003024468 | 3/2003 |
| WO | 2003077895 | 9/2003 |
| WO | 2003094927 | 11/2003 |
| WO | 2004084820 A2 | 10/2004 |
| WO | 2005041022 A1 | 5/2005 |
| WO | 2005081119 A2 | 9/2005 |
| WO | 2005081170 A2 | 9/2005 |
| WO | 2005081171 A2 | 9/2005 |
| WO | 2005081173 A1 | 9/2005 |
| WO | 2005110222 A1 | 11/2005 |
| WO | 2006022619 A2 | 3/2006 |
| WO | 2006022629 A1 | 3/2006 |
| WO | 2006022633 A1 | 3/2006 |
| WO | 2006022634 A1 | 3/2006 |
| WO | 2006022636 A1 | 3/2006 |
| WO | 2006022638 A1 | 3/2006 |
| WO | 2006044556 A2 | 4/2006 |
| WO | 2003101177 | 7/2006 |
| WO | 2006079124 A2 | 7/2006 |
| WO | 2006091918 A2 | 8/2006 |
| WO | 2006130901 A1 | 12/2006 |
| WO | 2007116226 A2 | 10/2007 |
| WO | 2007149533 A2 | 12/2007 |
| WO | 2008005761 A2 | 1/2008 |
| WO | 2008013324 A1 | 1/2008 |
| WO | 2008057213 A2 | 5/2008 |
| WO | 2008057384 A2 | 5/2008 |
| WO | 2008067245 A2 | 6/2008 |
| WO | 2008088490 A1 | 7/2008 |
| WO | 2008112078 A2 | 9/2008 |
| WO | 2008124478 A1 | 10/2008 |
| WO | 2009002455 A1 | 12/2008 |
| WO | 2009005960 A2 | 1/2009 |
| WO | 2009075925 A1 | 6/2009 |
| WO | 2009139846 A1 | 11/2009 |
| WO | 2009146119 A2 | 12/2009 |

(56) References Cited

FOREIGN PATENT DOCUMENTS

| | | |
|---|---|---|
| WO | 2009146121 A2 | 12/2009 |
| WO | 2010021879 A2 | 2/2010 |
| WO | 2010056718 A2 | 5/2010 |
| WO | 2010075350 A1 | 7/2010 |
| WO | 2010089304 A1 | 8/2010 |
| WO | 2010089305 A1 | 8/2010 |
| WO | 2010089306 A1 | 8/2010 |
| WO | 2010089307 A1 | 8/2010 |
| WO | 2010091102 A1 | 8/2010 |
| WO | 2010097796 A1 | 9/2010 |
| WO | 2010135646 A1 | 11/2010 |
| WO | 2010147659 A2 | 12/2010 |
| WO | 2011008520 A2 | 1/2011 |
| WO | 2011037607 A2 | 3/2011 |
| WO | 2011075687 A1 | 6/2011 |
| WO | 2011089600 A1 | 7/2011 |
| WO | 2011094352 A1 | 8/2011 |
| WO | 2011157402 A1 | 12/2011 |
| WO | 2012023964 A1 | 2/2012 |
| WO | 2012047800 A1 | 4/2012 |
| WO | 2012065556 A1 | 5/2012 |
| WO | 2012097064 A1 | 7/2012 |
| WO | 2012122520 A1 | 9/2012 |
| WO | 2012148252 A2 | 11/2012 |
| WO | 2012161670 A2 | 11/2012 |
| WO | 2012177963 A1 | 12/2012 |
| WO | 2013040712 A1 | 3/2013 |
| WO | 2013050309 A1 | 4/2013 |
| WO | 2013086372 A1 | 6/2013 |
| WO | 2013096769 A1 | 6/2013 |
| WO | 2013108262 A1 | 7/2013 |
| WO | 2013134548 A2 | 9/2013 |
| WO | 2013172833 A1 | 11/2013 |
| WO | 2013177565 A1 | 11/2013 |
| WO | 2014011488 A2 | 1/2014 |
| WO | 2014012084 A1 | 1/2014 |
| WO | 2014023834 A2 | 2/2014 |
| WO | 2014024201 A1 | 2/2014 |
| WO | 2014028607 A1 | 2/2014 |
| WO | 2014068007 A1 | 5/2014 |
| WO | 2014075135 | 5/2014 |
| WO | 2014075135 A1 | 5/2014 |
| WO | 2014099829 | 6/2014 |
| WO | 2014099829 A1 | 6/2014 |
| WO | 2014106263 A2 | 7/2014 |
| WO | 2014145049 A2 | 9/2014 |
| WO | 2014149535 | 9/2014 |
| WO | 2014149535 A1 | 9/2014 |
| WO | 2014149781 A1 | 9/2014 |
| WO | 2014152704 A1 | 9/2014 |
| WO | 2014162549 A1 | 10/2014 |
| WO | 2014162549 A1 | 10/2014 |
| WO | 2014164226 A2 | 10/2014 |
| WO | 2014179171 A1 | 11/2014 |
| WO | 2014187812 A1 | 11/2014 |
| WO | 2014190231 A1 | 11/2014 |
| WO | 2014202024 A1 | 12/2014 |
| WO | 2014209630 A2 | 12/2014 |
| WO | 2014209634 A1 | 12/2014 |

OTHER PUBLICATIONS

Vaidya, Anand et al., "Improving the management of diabetes in hospitalized patients: The result of a computer-based house staff training program", Diabetes Technology & Therapeutics, 2012, vol. 14, No. 7, pp. 610-618.
Lee, Joshua et al., "Indication-based ordering: A new paradigm for glycemic control in hospitalized inpatients", Journal of Diabetes Science and Technology, May 2008, vol. 2, Issue 3, pp. 349-356.
Nau, Konrad C. et al, "Glycemic Control in hospitalized patients not in intensive care: Beyond sliding-scale insulin", American Family Physician, May 1, 2010, vol. 81, No. 9, pp. 1130-1133.
International Search Report and Written Opinion for Application No. PCT/US2015/011559 dated Apr. 29, 2015.
International Search Report and Written Opinion for Application No. PCT/US2015/011086 dated Apr. 29, 2015.
International Search Report and Written Opinion for Application No. PCT/US2015/011574 dated Apr. 24, 2015.
International Search Report and Written Opinion for Application No. PCT/US2016/047806 dated Nov. 25, 2016.

* cited by examiner

New Patient Information

Demographic Information 208a

| | |
|---|---|
| Name: | John Doe |
| Height: | 5' 8" |
| Weight: | 210 |
| Date of Birth: | 4/10/1981 |
| Age: | 34 |
| Diabetes History: | Type I; 25 Years |
| Disease History: | ▼ |
| Clinical Attributes: | ▼ |
| Financial Attributes: | ▼ |
| Other: | ▼ |

∽ 116,146

BG History Data 208b

[ Manual ]  [ Download ]

SubQ Information 208c

Orderset Type: [Basal/Bolus + Correction ▼]   TDD: [54] units

Bolus Insulin: [Novolog ▼]   CF [1700]   ICR: [1:10]

Meal Plan: [Yes ▼]   Basal Insulin: [Lantus ▼]

Meal Bolus % of TDD: [50% ▼]   Basal % of TDD: [50% ▼]

Daily Meal Bolus Distribution:   Daily Basal Distribution: [1 Dose Per Day ▼]

Breakfast Bolus: [9] units   Basal Dose: [27] units

Lunch Bolus: [9] units   Basal Time: [21:00 ▼]

Dinner Bolus: [9] units

*Caution: Physician order required*   Target BG Range: [95 - 115] Mg/dL

[ Treatment ]∽ 300b

FIG. 2B

Current Patient (Subcutaneous) — 116,146

Name: John Doe    ID: 198
Diagnosis: T1 Diabetic    Date of Birth: 4/10/1981    — 208a

Insulin Dose and Outcome History

| Date | Bolus | Dose | BGnext |
|------|-------|------|--------|
| 5/20/14 | Dinner | 7u | 77 |
| 5/20/14 | Lunch | 5u | 142 |
| 5/20/14 | Breakfast | 6u | 102 |
| 5/19/14 | Dinner | 6u | 98 |
| 5/19/14 | Lunch | 5u | 123 |
| 5/19/14 | Breakfast | 6u | 89 |
| 5/18/14 | Dinner | 7u | 76 |
| 5/18/14 | Lunch | 5u | 115 |
| 5/18/14 | Breakfast | 6u | 95 |

— 208b

Basal Insulin: Lantus
Insulin Type: Novolog
Last BG: 77 mg/dl
BG Type: Breakfast
Basal Dose: 15 units (1 dose per day)
Next Meal Dose: 5 units — 208c

[Treatment] — 300b

FIG. 2C

DIABETES MANAGEMENT THERAPY ADVISOR

CROSS REFERENCE TO RELATED APPLICATIONS

This U.S. patent application is a continuation of, and claims priority under 35 U.S.C. § 120 from, U.S. patent application Ser. No. 17/454,054, filed on Nov. 8, 2021, which is a continuation of U.S. patent application Ser. No. 16/503,048, filed on Jul. 3, 2019, which is a continuation of U.S. patent application Ser. No. 15/851,733, filed on Dec. 21, 2017, which is a continuation of U.S. patent application Ser. No. 15/241,703, filed on Aug. 19, 2016, which claims priority under 35 U.S.C. § 119(e) to U.S. Provisional Application 62/207,613, filed on Aug. 20, 2015. The disclosures of these prior applications are considered part of the disclosure of this application and are hereby incorporated by reference in their entireties.

TECHNICAL FIELD

This disclosure relates to a diabetes management therapy advisor for identifying and optimizing personalized therapies for the treatment of Diabetes Mellitus.

BACKGROUND

According to the most recent data from the American Diabetes Association and CDC, more than 29 million Americans have diabetes. But even more importantly, another 86 million—or one in three—have pre-diabetes. Without effective intervention, it is estimated that 15%-20% of these individuals will develop diabetes within five years. The International Diabetes Federation reports the global incidence of diabetes at 387 million people. It is expected that this number will grow to 592 million people over the next 20 years.

Diabetics often have higher rates of cardiovascular, renal, gastrointestinal, neurological, thyroid diseases, and ophthalmological complications compared to people without diabetes. Patients with diabetes often may receive a wide array of medications including injectable long-acting and rapid-acting insulins, inhaled insulin, oral medications, and other injectable anti-diabetic medications. Among the different classes of medications, some medications are contraindicated for pregnancy or patients with severe kidney disease. Moreover, other medications which are appropriate for the treatment of Type 2 diabetes, are contraindicated for Type 1 diabetes.

SUMMARY

One aspect of the disclosure provides a method for determining a treatment dose for a treated patient. The method includes obtaining, at data processing hardware, training data for a plurality of patients of a patient population from memory hardware in communication with the data processing hardware. The training data includes training blood glucose history data and training patient-state information for each patient of the patient population. The training blood glucose history data includes treatment doses of insulin administered by the patients of the patient population and one or more outcome attributes associated with each treatment dose of insulin administered by the patients of the patient population. For each patient of the patient population, the method includes identifying, using the data processing hardware, one or more optimum treatment doses of insulin from the treatment doses of insulin yielding favorable outcome attributes. The method also includes receiving, at the data processing hardware, patient-state information for the treated patient. The method also includes determining, using the data processing hardware, a next recommended treatment dose of insulin for the treated patient based on one or more of the identified optimum treatment doses associated with the patients of the patient population having training patient-state information similar to the patient-state information for the treated patient. The method further includes transmitting the next recommended treatment dose to a portable device associated with the treated patient, the portable device displaying the next recommended insulin dose.

Implementations of the disclosure may include one or more of the following optional features. In some implementations, obtaining the training data includes obtaining the training data automatically at an end of a re-occurring configurable time interval. Obtaining the training data may include obtaining the training data immediately in response to a user input selecting an immediate start button displayed upon a display in communication with the data processing hardware. Obtaining the training data may also include obtaining the training data on a selected date.

In some examples, determining the next recommended treatment dose of insulin for the treated patient includes determining the treated patient requires insulin based on the patient-state information for the treated patient and receiving meal boluses of insulin previously administered by the treated patient during a scheduled time-interval. Determining a next recommended meal bolus during the scheduled time interval for the treated patient may be based on at least one of the identified optimum treatment doses associated with the scheduled time interval and the received meal boluses of insulin previously administered by the treated patient during the scheduled time interval. The scheduled time interval may include a pre-breakfast time interval, a pre-lunch time interval, a pre-dinner time interval, a bedtime time interval, or a midsleep time interval.

One or more outcome attributes of the training blood glucose history data may include a blood glucose percent error based on a function of a next scheduled blood glucose measurement and a blood glucose target range. The next scheduled blood glucose measurement may correspond to a blood glucose measurement occurring after administration of a corresponding treatment dose of insulin. Determining the next recommended treatment dose of insulin for the treated patient may include determining the treated patient requires insulin based on the patient-state information for the treated patient and receiving basal doses of insulin previously administered by the treated patient. Determining a next recommended basal dose for the treated patient may be based on at least one of the identified optimum treatment doses and the received basal doses of insulin previously administered by the treated patient.

In some examples, the method includes transmitting the next recommended treatment dose of insulin to an administration device in communication with the data processing hardware. The administration device may include a doser and an administration computing device in communication with the doser. The administration computing device may cause the doser to administer insulin specified by the next recommended treatment dose of insulin. Determining the next recommended treatment dose for the treatment patient may include determining anti-diabetic medications are usable for treating the treated patient based on the patient-state information for the treated patient, receiving a glycated hemoglobin measurement of the patient, and determining an anti-diabetes medication regimen for the treated patient based on the glycated hemoglobin measurement and the training data.

The treatment doses of the training data may correspond to anti-diabetes medication dose-combinations administered by patients of the patient population. The outcome attributes of the training data may correspond to a glycated hemoglobin measurement associated with each anti-diabetes medication regimen. The patient-state information may include a plurality of patient-state attributes associated with the patient. The patient-state attributes may include one or more of an age, a gender, a medical history, a body mass index, a medical history, risk factors, and/or financial attributes.

Another aspect of the disclosure provides a system for determining a treatment dose for a treated patient. The system includes a dosing controller including data processing hardware and memory hardware in communication with the data processing hardware. The dosing controller obtains training data for a plurality of patients of a patient population from the memory hardware. The training data includes training blood glucose history data and training patient-state information for each patient of the patient population. The training blood glucose history data includes treatment doses of insulin administered by the patients of the patient population and one or more outcome attributes associated with each treatment dose of insulin administered by the patients of the patient population. For each patient of the patient population, the system includes identifying one or more optimum treatment doses of insulin from the treatment doses of insulin yielding favorable outcome attributes and receiving patient-state information for the treated patient. The system also includes determining a next recommended treatment dose of insulin for the treated patient based on one or more of the identified optimum treatment doses associated with the patients of the patient population having training patient-state information similar to the patient-state information for the treated patient. The system further includes transmitting the next recommended treatment dose to a portable device associated with the treated patient, the portable device displaying the next recommended insulin dose.

This aspect may include one or more of the following optional features. In some implementations, obtaining the training data includes obtaining the training data automatically at an end of a re-occurring configurable time interval. Obtaining the training data may include obtaining the training data immediately in response to a user input selecting an immediate start button displayed upon a display in communication with the data processing hardware. Obtaining the training data may further include obtaining the training data on a selected date.

In some examples, determining the next recommended treatment dose of insulin for the treated patient comprises determining the treated patient requires insulin based on the patient-state information for the treated patient and receiving meal boluses of insulin previously administered by the treated patient during a scheduled time-interval. Determining a next recommended meal bolus during the scheduled time interval for the treated patient may be based on at least one of the identified optimum treatment doses associated with the scheduled time interval and the received meal boluses of insulin previously administered by the treated patient during the scheduled time interval. The scheduled time interval may include a pre-breakfast time interval, a pre-lunch time interval, a pre-dinner time interval, a bedtime time interval, or a midsleep time interval. The one or more outcome attributes of the training blood glucose history data may include a blood glucose percent error based on a function of a next scheduled blood glucose measurement and a blood glucose target range. The next scheduled blood glucose measurement may correspond to a blood glucose measurement occurring after administration of a corresponding treatment dose of insulin.

Determining the next recommended treatment dose of insulin for the treated patient may include determining the treated patient requires insulin based on the patient-state information for the treated patient and receiving basal doses of insulin previously administered by the treated patient. Determining a next recommended basal dose for the treated patient may be based on at least one of the identified optimum treatment doses and the received basal doses of insulin previously administered by the treated patient.

In some examples, the dosing controller may transmit the next recommended treatment dose of insulin to an administration device in communication with the dosing controller. The administration device may include a doser and an administration device in communication with the doser. The administration computing device may cause the doser to administer insulin specified by the next recommended treatment dose of insulin.

In some implementations, determining the next recommended treatment dose for the treated patient includes determining anti-diabetic medications are usable for treating the treated patient based on the patient-state information for the treated patient, receiving a glycated hemoglobin measurement of the patient, and determining an anti-diabetes medication regimen for the treated patient based on the glycated hemoglobin measurement and the training data.

The treatment doses of the training data may correspond to anti-diabetes medication dose-combinations administered by patients of the patient population. The outcome attributes of the training data may correspond to a glycated hemoglobin measurement associated with each anti-diabetes medication regimen. The patient-state information may include a plurality of patient-state attributes associated with the patient. The patient-state attributes may include one or more of an age, a gender, a medical history, a body mass index, a medical history, risk factors, and/or financial attributes.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 2B and 2C are schematic views of an exemplary display for inputting patient information.

Like reference symbols in the various drawings indicate like elements.

DETAILED DESCRIPTION

Diabetes requires early, continuous, effective, and regular treatment to significantly delay, and in some instances eliminate, the progression of the disease. For non-specialist healthcare providers, managing diabetes can be an extremely complex process. Patients with diabetes are often prescribed a large number of different medications for dyslipidemia, hypertension, and control of blood glucose. Diuretic medications often used to treat heart failure, blood pressure, and other kidney disorders, may have an unintended side effect that contributes to hypoglycemia. Healthcare professions must weigh effects and potential pharmacodynamics and pharmacokinetic interactions of concomitant medications.

Figure 1A:
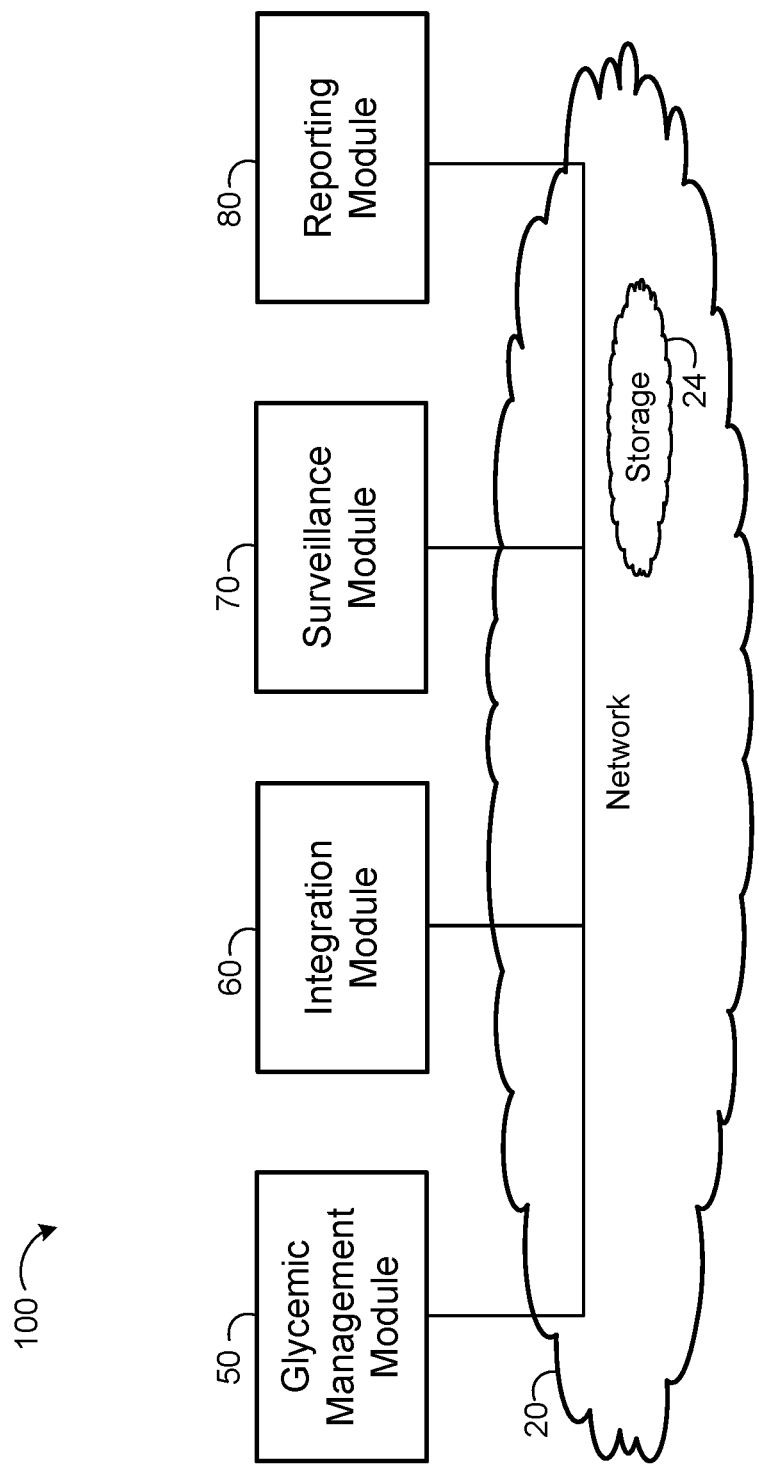
FIG. 1A is a schematic view of an exemplary system for recommending treatment doses for a patient.
Figure 1B:
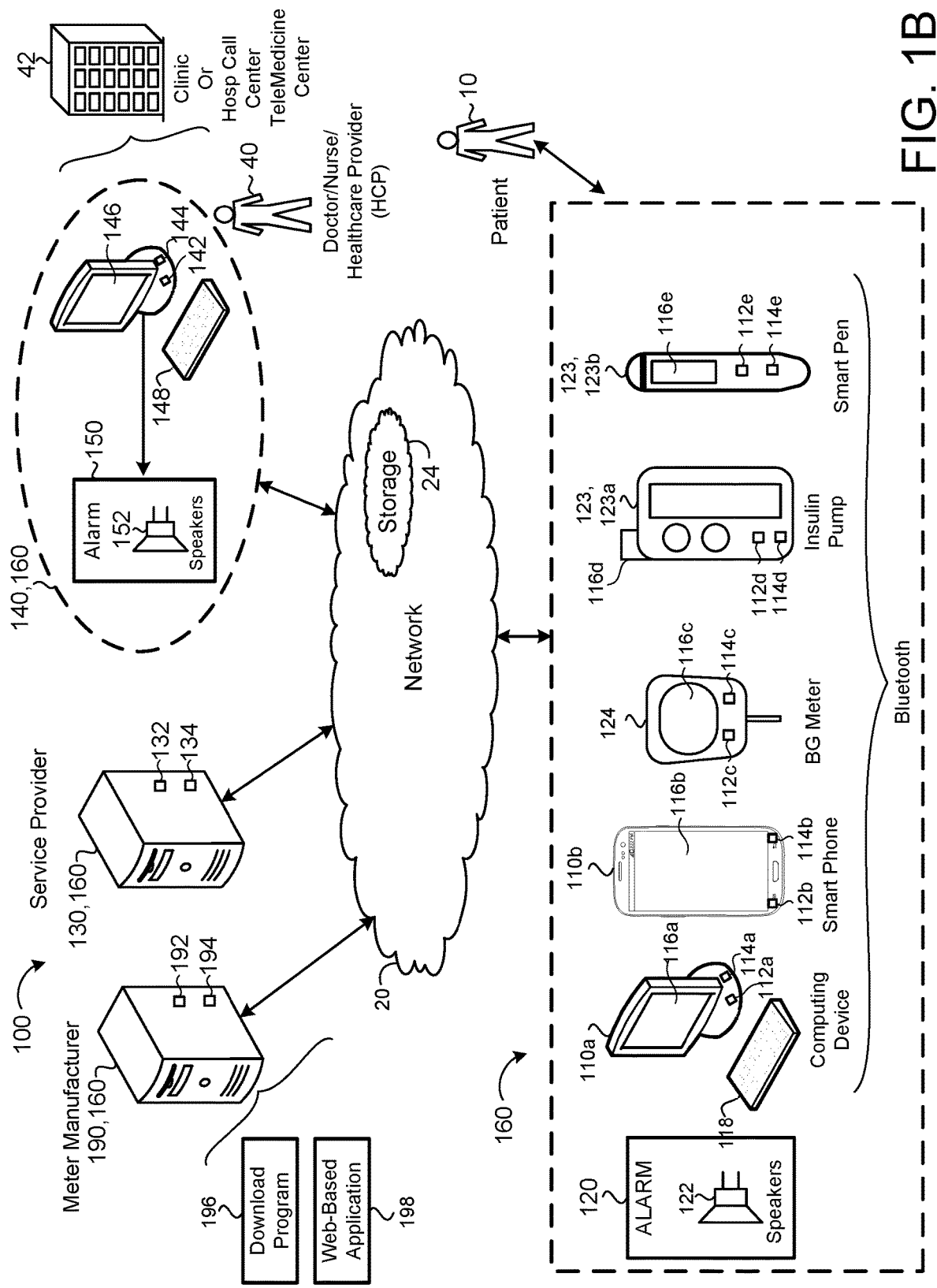
FIG. 1B is a schematic view of an exemplary system for recommending treatment doses for a patient.
Figure 1C:
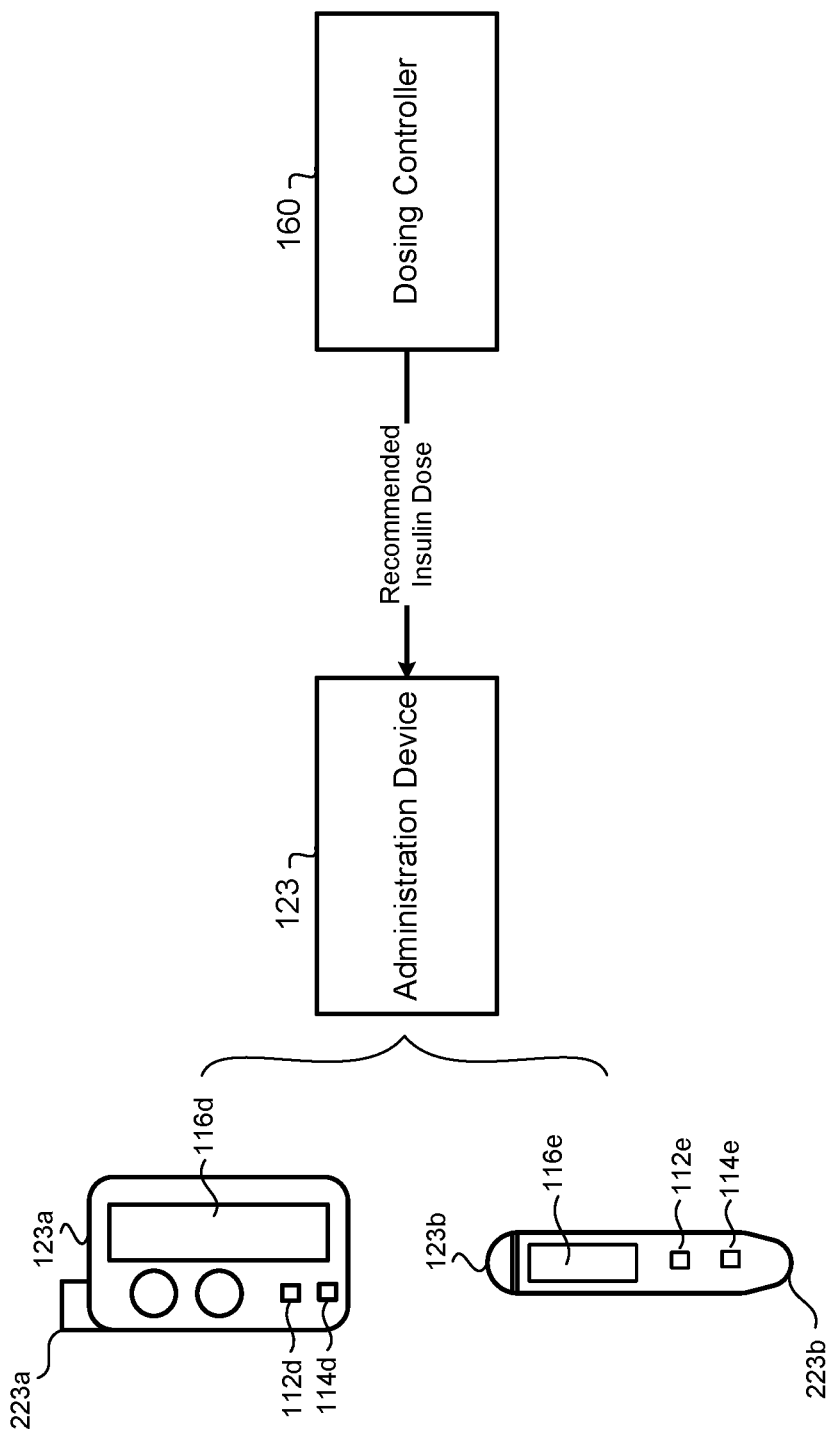
FIG. 1C is a schematic view of an exemplary administration device in communication with a dosing controller.

Referring to FIGS. 1A-1C, in some implementations, a clinical decision support system 100 analyzes inputted patient condition parameters for a patient 10 and calculates a personalized dose of insulin to bring and maintain the patient's blood glucose level into a target range $BG_{TR}$. As used herein, the patient 10 may refer to an outpatient that may be located at some remote location, such as the patient's 10 residence or place of employment, or to an inpatient located at a clinic 42 or hospital. Moreover, the system 100 monitors the glucose levels of a patient 10 and calculates a recommended subcutaneous insulin dose to bring the patient's blood glucose into the preferred target range $BG_{TR}$ over a recommended period of time. In some implementations, the system 100 monitors glycated hemoglobin (hereinafter 'A1c') levels of a patient 10 and calculates a recommended dose of one or more Anti-Diabetes Medications (ADMs) to significantly delay, and in some instances eliminate, the progression of diabetes in the patient 10. As used herein, ADMs refer to non-insulin medications that may be administered to the patient. A qualified and trained healthcare professional 40 may use the system 100 along with clinical reasoning to determine the proper dosing (e.g., insulin dosing, ADM dosing, or a combination of the two) administered to a patient 10. Therefore, the system 100 is a glycemic management tool for evaluation of a patient's current and cumulative blood glucose value BG, or current and cumulative A1c level, while taking into consideration the patient's information such as age, weight, and height. The system 100 may also consider other information such as carbohydrate content of meals and/or insulin doses being administered to the patient 10, e.g., long-acting insulin doses for basal insulin and rapid-acting insulin doses for meal boluses and correction boluses. Based on those measurements (that may be stored in non-transitory memory 24, 114, 144), the system 100 recommends a subcutaneous basal and bolus insulin dosing recommendation or prescribed dose to adjust and maintain the blood glucose level towards a configurable (based on the patient's information) physician's determined blood glucose target range $BG_{TR}$. The system 100 also considers a patient's insulin sensitivity or improved glycemic management and outcomes. In some examples, the system 100 recommends an ADM dosing recommendation treatment to adjust and maintain the A1c level of the patient 10 towards a configurable (based on the patient's information) physician's determined A1c target range $A1c_{TR}$.

The system 100 may take into account pertinent patient information such as patient-state information and blood glucose BG history data associated with the patient 10. The system 100 may include a domain knowledge base including information about diabetes (that may be stored in non-transitory memory 24, 114, 144), including pertinent information about Type 1 diabetes mellitus (hereinafter 'DM1') and Type 2 diabetes mellitus (hereinafter 'DM2'). The domain knowledge base may also include information associated with effects and potential pharmacodynamics and pharmacokinetic interactions of concomitant medications. Based on the information of the domain knowledge base and the patient-state information and/or the BG history data associated with the patient 10, the system 100 may select a personalized diabetes treatment therapy for glycemic control of the patient 10. The system 100 may also store (in non-transitory memory 24, 114, 144) training blood glucose BG data and patient-state information for a patient population, and use the training BG data for patients of the patient population that have similar patient-state attributes as the patient 10 to adjust a subcutaneous basal and bolus insulin dosing recommendation (or an ADM dosing recommendation) associated with the patient 10.

Finally, the system 100 provides a reporting platform for reporting the recommendations, adjustments, or prescribed dose(s) to the user 40 and the patient 10. In addition, the system 100 provides faster, more reliable, and more efficient insulin administration than a human monitoring the insulin administration. The system 100 reduces human oversight in prescribing medications that may contribute to unintended side effects of hypoglycemia or hyperglycemia due to the system's capability of accessing the information of the domain knowledge base. The system 100 reduces the probability of human error and insures consistent treatment, due to the system's capability of storing and tracking the patient's blood glucose levels BG, which may be used for statistical studies. The system 100 provides a meal-by-meal adjustment of Meal Boluses without carbohydrate counting, by providing a dedicated subprogram that adjusts meal boluses based on the immediately preceding meal bolus and the BG that followed it. The system 100 provides a meal-by-meal adjustment of Meal Boluses with carbohydrate counting by providing a dedicated subprogram that adjusts meal boluses based a Carbohydrate-to-Insulin Ratio (CIR) that is adjusted at each meal, based on the CIR used at the immediately preceding meal bolus and the BG that followed it.

Hyperglycemia is a condition that exists when blood sugars are too high. While hyperglycemia is typically associated with diabetes, this condition can exist in many patients who do not have diabetes, yet have elevated blood sugar levels caused by trauma or stress from surgery and other complications from hospital procedures. Insulin therapy is used to bring blood sugar levels back into a normal range.

Hypoglycemia may occur at any time when a patient's blood glucose level is below a preferred target. Appropriate management of blood glucose levels for critically ill patients reduces co-morbidities and is associated with a decrease in infection rates, length of hospital stay, and death. The treatment of hyperglycemia may differ depending on whether or not a patient has been diagnosed with DM1, DM2, gestational diabetes mellitus, or non-diabetic stress hyperglycemia. The blood glucose target range $BG_{TR}$ is defined by a lower limit, i.e., a low target $BG_{TRL}$ and an upper limit, i.e., a high target $BG_{TRH}$.

Diabetes Mellitus has been treated for many years with insulin. Some recurring terms and phrases are described below:

Injection: Administering insulin by means of manual syringe or an insulin "pen," with a portable syringe named for its resemblance to the familiar writing implement.

Infusion: Administering insulin in a continuous manner by means of an insulin pump for subcutaneous insulin apparatus 123, 123a capable of continuous administration.

Basal-Bolus Therapy: Basal-bolus therapy is a term that collectively refers to any insulin regimen involving basal insulin and boluses of insulin.

Basal Insulin: Insulin that is intended to metabolize the glucose released by a patient's the liver during a fasting state. Basal insulin is administered in such a way that it maintains a background level of insulin in the patient's blood, which is generally steady but may be varied in a programmed manner by an insulin pump 123a. Basal insulin is a slow, relatively continuous supply of insulin throughout the day and night that provides the low, but present, insulin concentration necessary to balance glucose consumption (glucose uptake and oxidation) and glucose production (glucogenolysis and gluconeogenesis). A patient's Basal insulin needs are usually about 10 to 15 mU/kg/hr and account for 30% to 50% of the total daily insulin needs; however, considerable variation occurs based on the patient 10.

Bolus Insulin: Insulin that is administered in discrete doses. There are two main types of boluses, Meal Bolus and Correction Bolus.

Meal Bolus: Taken just before a meal in an amount which is proportional to the anticipated immediate effect of carbohydrates in the meal entering the blood directly from the digestive system. The amounts of the Meal Boluses may be determined and prescribed by a physician 40 for each meal during the day, i.e., breakfast, lunch, and dinner. Alternatively, the Meal Bolus may be calculated in an amount generally proportional to the number of grams of carbohydrates in the meal. The amount of the Meal Bolus is calculated using a proportionality constant, which is a personalized number called the Carbohydrate-to-Insulin Ratio (CIR) and calculated as follows:

$$\text{Meal Insulin Bolus} = \{\text{grams of carbohydrates in the meal}\}/CIR \quad (1)$$

Correction Bolus CB: Injected immediately after a blood glucose measurement; the amount of the correction bolus is proportional to the error in the BG (i.e., the bolus is proportional to the difference between the blood glucose measurement BG and the patient's personalized Target blood glucose $BG_{Target}$). The proportionality constant is a personalized number called the Correction Factor, CF, and is calculated as follows:

$$CB=(BG-BG_{Target})/CF \quad (2)$$

A Correction Bolus CB is generally administered in a fasting state, after the previously consumed meal has been digested. This often coincides with the time just before the next meal.

In some implementations, blood glucose measurements BG are aggregated using an exponentially-weighted moving average $EMA_t$ as a function for each modal day's time interval BG. The EMAt is calculated as follows:

$$EMA_t = \alpha(BG_t) + (1-\alpha)EMA_{t-1}, \quad (3)$$

wherein:

$$\alpha = 2/(n+1),$$

wherein n is the number of equivalent days averaged. In other embodiments, an arithmetic moving average is utilized that calculates the sum of all BG values in n days divided by a total count (n) of all values associated with the arithmetic average.

There are several kinds of Basal-Bolus insulin therapy including Insulin Pump therapy and Multiple Dose Injection therapy:

Insulin Pump Therapy: An insulin pump 123a is a medical device used for the administration of insulin in the treatment of diabetes mellitus, also known as continuous subcutaneous insulin infusion therapy. The device includes: a pump, a disposable reservoir for insulin, and a disposable infusion set. The pump 123a is an alternative to multiple daily injections of insulin by insulin syringe or an insulin pen and allows for intensive insulin therapy when used in conjunction with blood glucose monitoring and carbohydrate counting. The insulin pump 123a is a battery-powered device about the size of a pager. It contains a cartridge of insulin, and it pumps the insulin into the patient via an "infusion set", which is a small plastic needle or "canula" fitted with an adhesive patch. Only rapid-acting insulin is used.

Multiple Dose Injection (MDI): MDI involves the subcutaneous manual injection of insulin several times per day using syringes or insulin pens 123b. Meal insulin is supplied by injection of rapid-acting insulin before each meal in an amount proportional to the meal. Basal insulin is provided as a once, twice, or three time daily injection of a dose of long-acting insulin. Other dosage frequencies may be available. Advances continue to be made in developing different types of insulin, many of which are used to great advantage with MDI regimens:

Long-acting insulins are non-peaking and can be injected as infrequently as once per day. These insulins are widely used for Basal Insulin. They are administered in dosages that make them appropriate for the fasting state of the patient, in which the blood glucose is replenished by the liver to maintain a steady minimum blood glucose level.

Rapid-acting insulins act on a time scale shorter than natural insulin. They are appropriate for boluses.

The clinical decision support system 100 includes a glycemic management module 50, an integration module 60, a surveillance module 70, and a reporting module 80. Each module 50, 60, 70, 80 is in communication with the other modules 50, 60, 70, 80 via a network 20. In some examples, the network 24 (discussed below) provides access to cloud computing resources that allows for the performance of services on remote devices instead of the specific modules 50, 60, 70, 80. The glycemic management module 50 executes a process 200 (e.g., an executable instruction set) on a processor 112, 132, 142 or on the cloud computing resources. The integration module 60 allows for the interaction of users 40 and patients 10 with the system 100. The integration module 60 receives information inputted by a user 40 and allows the user 40 to retrieve previously inputted information stored on a storage system (e.g., one or more of cloud storage resources 24, a non-transitory memory 144 of a clinic's electronic medical system 140, a non-transitory memory 114 of the patient device 110, or other non-transitory storage media in communication with the integration module 60). Therefore, the integration module 60 allows for the interaction between the users 40, patients 10, and the system 100 via a display 116, 146. In some examples, integration module 60 allows the user 40 or patient 10 to input blood glucose history data 208b associated with the patient 10 for storage on the storage system 24, 144, 114. The surveillance module 70 considers patient state information 208a received from a user 40 via the integration module 60 and information received from a glucometer 124 that measures a patient's blood glucose value BG and determines if the patient 10 is within a threshold blood glucose value $BG_{TH}$. In some examples, the surveillance module 70 alerts the user 40 if a patient's blood glucose values BG are not within a threshold blood glucose value $BG_{TH}$. The surveillance module 70 may be preconfigured to alert the user 40 of other discrepancies between expected values and actual values based on pre-configured parameters (discussed below). For example, when a patient's blood glucose value BG drops below a lower limit of the threshold blood glucose value $BG_{THL}$. The reporting module 80 may be in communication with at least one display 116, 146 and provides information to the user 40 determined using the glycemic management module 50, the integration module 60, and/or the surveillance module 70. In some examples, the reporting module 80 provides a report that may be displayed on a display 116, 146 and/or is capable of being printed.

The system 100 is configured to evaluate a glucose level and nutritional intake of a patient 10. Based on the evaluation and analysis of the data, the system 100 calculates an insulin dose, which is administered to the patient 10 to bring and maintain the blood glucose level of the patient 10 into the blood glucose target range $BG_{TR}$. The system 100 may be applied to various devices, including, but not limited to, subcutaneous insulin infusion pumps 123a, insulin pens 123b, glucometers 124, continuous glucose monitoring systems, and glucose sensors.

In some implementations, the system 100 considers outcome data associated with an insulin dose administered to the patient 10. The outcome data may include a next scheduled blood glucose measurement BGnext showing the effect of the insulin dose previously administered to the patient 10. Generally, the BGnext occurs a sufficient amount of time (e.g., four to six hours) after the insulin dose is administered to the patient after the effects of the insulin and food are both complete so that the BGnext indicates the precision of the recommended dose. For example, the system 100 may adjust a next recommended insulin dose by increasing the dose when the BGnext is greater than a target center $BG_{TC}$ of the blood glucose target range $BG_{TR}$, or decreasing the dose when the BGnext is less than the target center $BG_{TC}$. The next recommended insulin dose may include a next scheduled meal bolus after the administered insulin dose or a meal bolus associated with the administered insulin dose, but on the next day.

In some examples the clinical decision support system 100 includes a network 20, a patient device 110, a dosing controller 160, a service provider 130, and a meter manufacturer provider 160. The patient device 110 may include, but is not limited to, desktop computers 110a or portable electronic device 110b (e.g., cellular phone, smartphone, personal digital assistant, barcode reader, personal computer, or a wireless pad) or any other electronic device capable of sending and receiving information via the network 20. In some implementations, one or more of the patient's glucometer 124, insulin pump 123a, or insulin pen 123b are capable of sending and receiving information via the network 20.

The patient device 110a, 110b includes a data processor 112a, 112b (e.g., a computing device that executes instructions), and non-transitory memory 114a, 114b and a display 116a, 116b (e.g., touch display or non-touch display) in communication with the data processor 112. In some examples, the patient device 110 includes a keyboard 118, speakers 212, microphones, mouse, and a camera.

The glucometer 124, insulin pump 123a, and insulin pen 123b associated with the patient 10 include a data processor 112c, 112d, 112e (e.g., a computing device that executes instructions), and non-transitory memory 114c, 114d, 114e and a display 116c, 116d, 116e (e.g., touch display or non-touch display in communication with the data processor 112c, 112d, 112e.

The meter manufacturer provider 190 may include may include a data processor 192 in communication with non-transitory memory 194. The data processor 192 may execute a proprietary download program 196 for downloading blood glucose BG data from the memory 114c of the patient's glucometer 124. In some implementations, the proprietary download program 196 is implemented on the health care provider's 140 computing device 142 or the patient's 10 device 110a for downloading the BG data from memory 114c. In some examples, the download program 196 exports a BG data file for storage in the non-transitory memory 24, 114, 144. The data processor 192 may further execute a web-based application 198 for receiving and formatting BG data transmitted from one or more of the patient's devices 110a, 110b, 124, 123a, 123b and storing the BG data in non-transitory memory 24, 114, 144.

The service provider 130 may include a data processor 132 in communication with non-transitory memory 134. The service provider 130 provides the patient 10 with a process 200 (see FIG. 2A) (e.g., a mobile application, a web-site application, or a downloadable program that includes a set of instructions) executable on a processor 112, 132, 142, 192 of the dosing controller 160 and accessible through the network 20 via the patient device 110, health care provider electronic medical record systems 140, portable blood glucose measurement devices 124 (e.g., glucose meter or glucometer), or portable administration devices 123a, 123b.

Figure 2A:
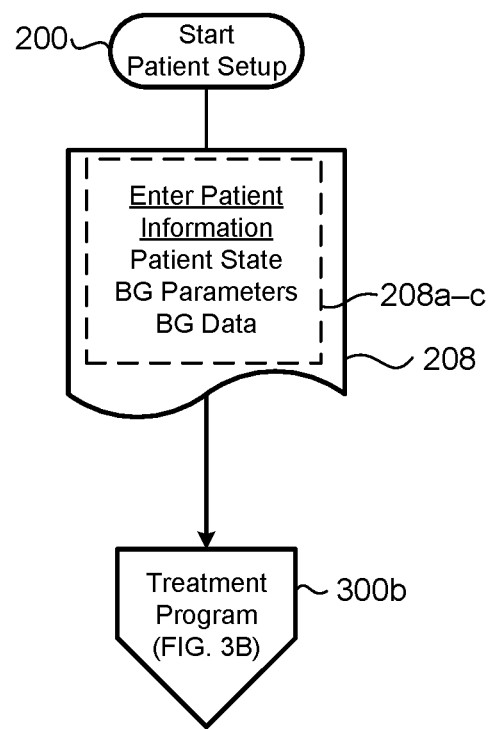
FIG. 2A is a schematic view of an exemplary process for starting a patient treatment program for a patient.

In some implementations, a health care provider medical record system 140 is located at a clinic 42 (or a doctor's office) and includes a data processor 142, a non-transitory memory 144, and a display 146 (e.g., touch display or non-touch display). The transitory memory 144 and the display 146 are in communication with the data processor 142. In some examples, the health care provider electronic medical system 140 includes a keyboard 148 in communication with the data processor 142 to allow a user 40 to input data, such as patient-state information 208a (FIGS. 2A-2C). The non-transitory memory 144 maintains patient records capable of being retrieved, viewed, and, in some examples, modified and updated by authorized hospital personal on the display 146.

The dosing controller 160 is in communication with the glucometer 124, insulin administration device 123a, 123b and includes a computing device 112, 132, 142 and non-transitory memory 114, 134, 144 in communication with the computing device 112, 132, 142. The dosing controller 160 executes the process 200. The dosing controller 160 stores patient related information retrieved from the glucometer 124 to determine an insulin dose rate IRR based on the received blood glucose measurement BG. The dosing controller 160 may store blood glucose BG history data 208b associated with the patient 10 that includes treatment doses and outcome attributes associated with each treatment dose administered by the patient. For example, the treatment dose may include the insulin dose rate IRR administered to the patient 10 and the outcome attribute may include the BGnext associated with the administered IRR. In other examples, the treatment dose may include one or more ADMs administered to the patient 10 and the outcome attribute may include a next scheduled A1c level associated with the administered ADMs.

Referring to FIG. 1C., in some implementations, the insulin device 123 (e.g., administration device), in communication with the dosing controller 160, is capable of executing instructions for administering insulin according to a subcutaneous insulin treatment program selected by the dosing controller 160. The administration device 123 may include the insulin pump 123a or the pen 123b. The administration device 123 is in communication with the glucometer 124 and includes a computing device 112d, 112e and non-transitory memory 114d, 114e in communication with the computing device 112d, 112e. The administration device 123 includes a doser 223a, 223b in communication with the administration computing device 112d, 112e for administering insulin to the patient 10. For instance, the doser 223a of the insulin pump 123a includes an infusion set including a tube in fluid communication with an insulin reservoir and a cannula inserted into the patient's 10 body and secured via an adhesive patch. The doser 223b of the pen 123b includes a needle for insertion into the patients 10 for administering insulin from an insulin cartridge. The administration device 123 may receive a subcutaneous insulin treatment program selected by and transmitted from the dosing controller 160, while the administration computing device 112d, 112e may execute the subcutaneous insulin treatment program. In some examples, the dosing controller 160 executes on the administration computing device 112d, 112e. Executing the subcutaneous insulin treatment program by the administration computing device 112d, 112e causes the doser 223a, 223b to administer doses of insulin specified by the subcutaneous insulin treatment program. For instance, units for the doses of insulin may be automatically set or dialed in by the administration device 123a, 123b and administered via the doser 223a, 223b to the patient 10. Accordingly, the administration devices 123a, 123b may be "smart" administration devices capable of communicating with the dosing controller 160, or implementing the dosing controller 160, to populate recommended doses of insulin for administering to the patient 10.

The network 20 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 20 may include one or more of a Wide Area Network (WAN), a Local Area Network (LAN), and a Personal Area Network (PAN). In some examples, the network 20 includes a combination of data networks, telecommunication networks, and a combination of data and telecommunication networks. The patient device 110, the service provider 130, and the hospital electronic medical record system 140 communicate with each other by sending and receiving signals (wired or wireless) via the network 20. In some examples, the network 20 provides access to cloud computing resources, which may be elastic/on-demand computing and/or storage resources 24 available over the network 20. The term 'cloud' services generally refers to a service performed not locally on a user's device, but rather delivered from one or more remote devices accessible via one or more networks 20.

Figure 2D:
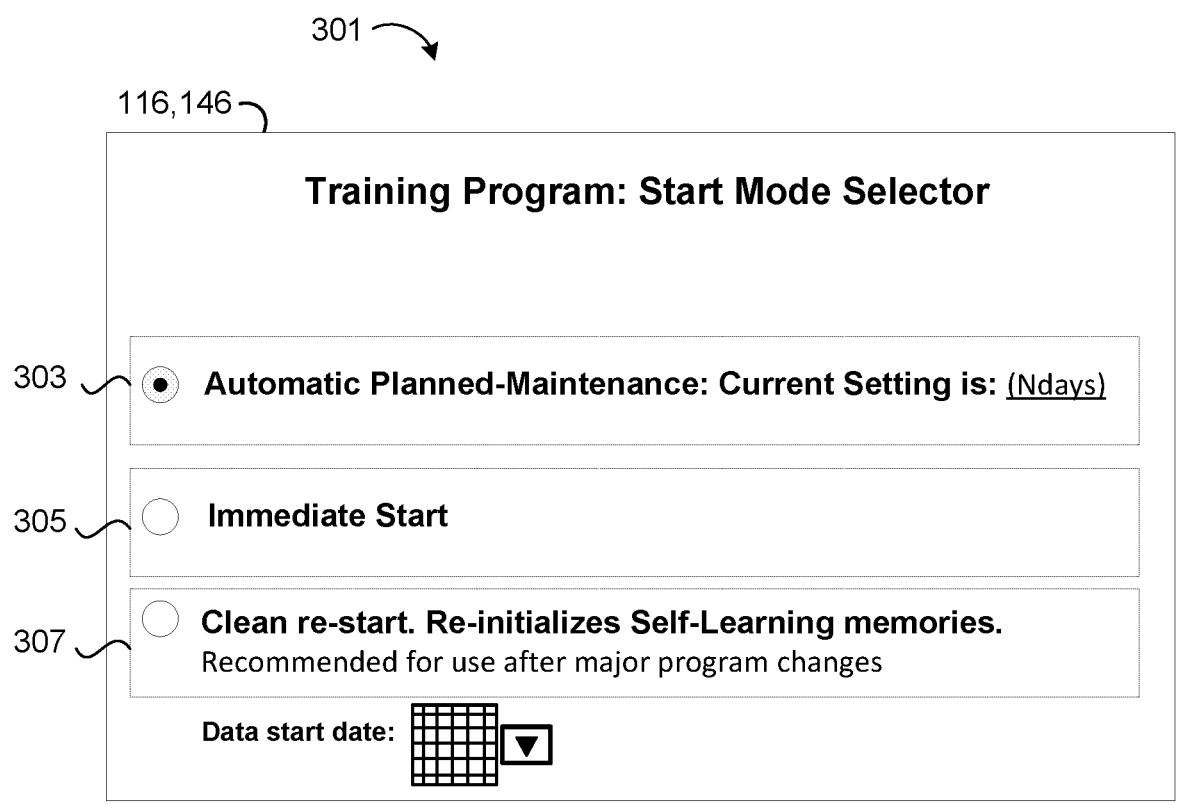
FIG. 2D is a schematic view of an exemplary display for selecting a start mode of a training program.
Figure 3A:
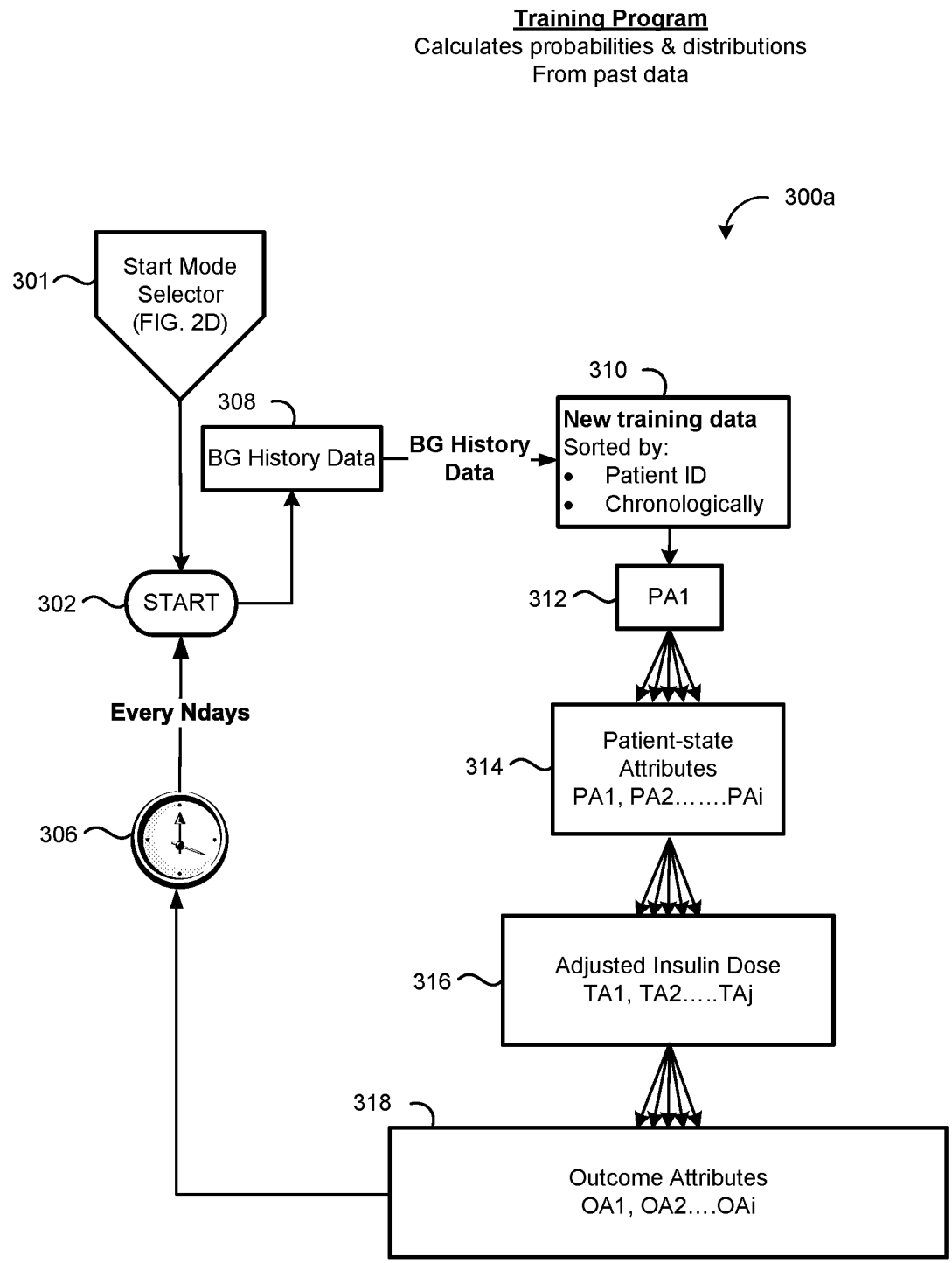
FIG. 3A is a schematic view of an exemplary patient training program for adjusting doses of insulin.
Figure 3B:
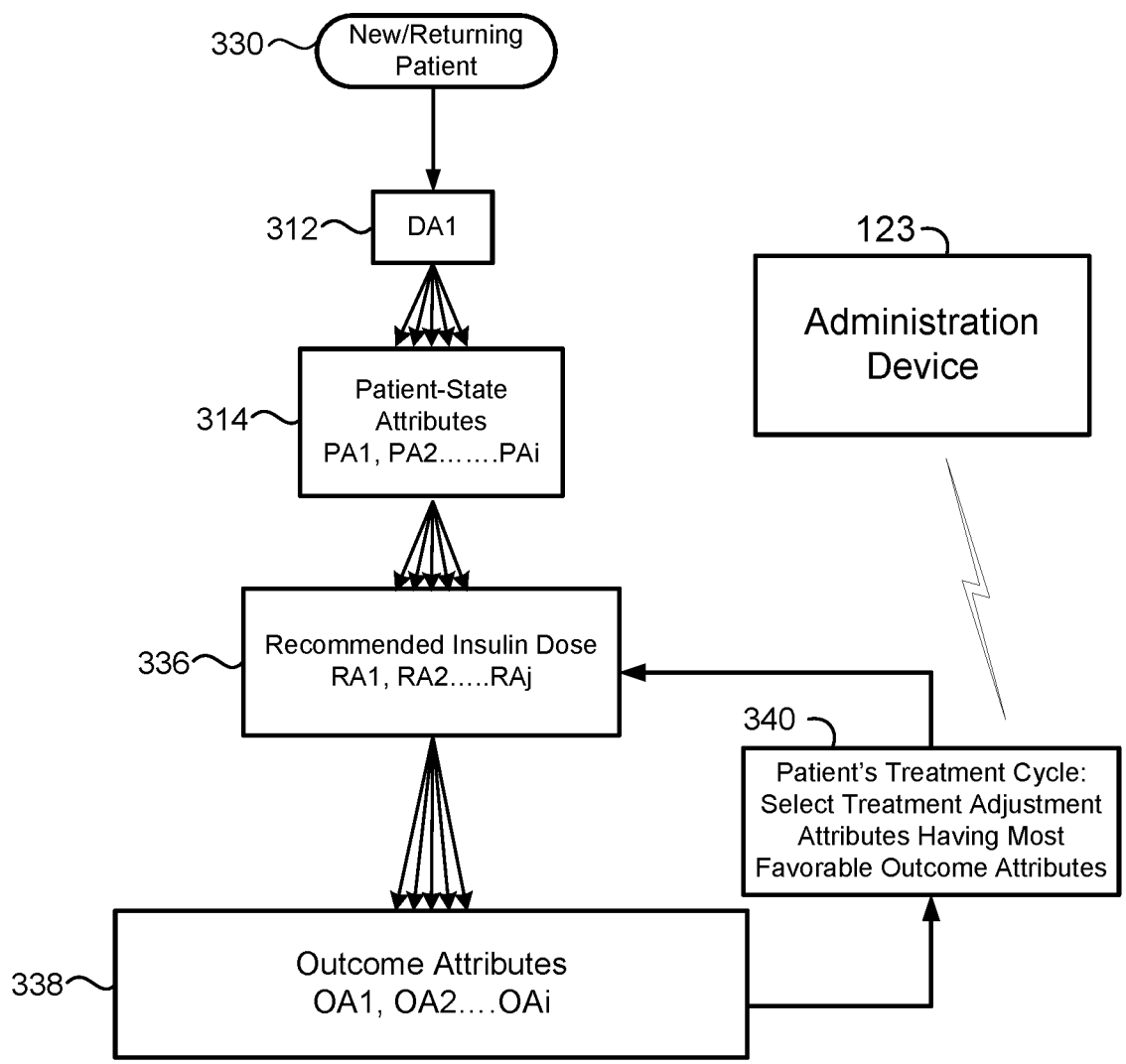
FIG. 3B is a schematic view of an exemplary patient treatment program using training data for determining an optimum dose of insulin.

Referring to FIGS. 1B and 2A-2D, the process 200 receives parameters (e.g., patient condition parameters) inputted via the client device 110, the service provider 130, and/or the clinic system 140, analyzes the inputted parameters and starts a patient treatment program 300b (FIG. 3B). Moreover, FIG. 2D shows a start mode selector 301 for starting a training program 300a that may be run at calendar intervals. The training program 300a enables the program to train itself to perform more effectively. To accomplish this, it retrieves a set of new training data 308 from the BG history data 208b and processes it to learn an up-to-date predictive model capable of predicting glycemic variables for a wide number of patient-profiles. From the training data 308, the training program 300a uses patient-state information 208a, BG history data 208b, and/or SubQ information 208c to tabulate counts and calculate probabilities, averages, regression functions, and/or other statistical data that may be saved (in the non-transitory memory 114, 134, 144). After the training run is complete, the probabilities and other statistical data are available for use by the treatment program 300b to predict an optimum treatment dose for the patient 10 that will yield a favorable outcome attribute. For example, the treatment program 300b may adjust a recommended dose of insulin for a SubQ meal bolus adjustment program 400a (FIG. 4A) or a SubQ basal adjustment program 400b (FIG. 4B) to bring and maintain a patient's blood glucose level BG as close to a target center $BG_{TC}$ of a preferred target range $BG_{TR}$.

In some implementations, before the process 200 begins to receive the parameters, the process 200 may receive a username and a password (e.g., at a login screen displayed on the display 116, 146) to verify that a qualified and trained healthcare professional 40 is initiating the process 200 and entering the correct information that the process 200 needs to accurately administer insulin to the patient 10. The system 100 may customize the login screen to allow a user 40 to reset their password and/or username. Moreover, the system 100 may provide a logout button (not shown) that allows the user 40 to log out of the system 100. The logout button may be displayed on the display 116, 146 at any time during the execution of the process 200.

The clinical decision support system 100 may include an alarm system 120 that alerts a user 40 when the patient's blood glucose level BG is outside the target range $BG_{TR}$. The alarm system 120 may produce an audible sound via speaker 122 in the form of a beep or some like audio sounding mechanism. In some examples, the alarm system 120 displays a warning message or other type of indication on the display 116a-e of the patient device 110 to provide a warning message. The alarm system 120 may also send the audible and/or visual notification via the network 20 to the clinic system 140 (or any other remote station) for display on the display 146 of the clinic system 140 or played through speakers 152 of the clinic system 140.

For commencing the training program 300a or the patient treatment program 300b, the process prompts a user 40 to input patient information 208a-c at block 208. The user 40 may input the patient information 208a-c, for example, via the user device 110 or via the health care provider medical record system 140 located at a clinic 42 (or a doctor's office). The user 40 may input new patient information 208a-c as shown in FIG. 2B. The process 200 may retrieve the patient information 208a-c from the non-transitory memory 144 of the clinic's electronic medical system 140 or the non-transitory memory 114 of the patient device 110 (e.g., where the patient information 208a-c was previously entered and stored). The patient information 208a-c may include, but is not limited to, patient-state information 208a, BG history data 208b (e.g., BG data), and SubQ information 208c (e.g., BG parameters) associated with the patient 10.

Referring to FIGS. 2A and 2C, the patient-state information 208a (e.g., demographic information (FIG. 2B)) for the patient 10 may include one or more patient-state attributes associated with the patient 10. The patient-state attributes are associated with attributes that do not change, change slowly, or change infrequently. For example, the patient-state information 208a may include, but is not limited to a patient's name, a patient's identification number (ID), a patient's height, weight, date of birth, diabetes history, disease history, clinical attributes, financial attributes, and any other relevant information. The disease history may include a list of all diseases of the patient 10 and a list of all medications prescribed for treating those diseases. Information in the disease history may indicate whether the patient 10 has important comorbidities that may dictate the personalized diabetes treatment therapy prescribed to the patient 10. The clinical attributes may include all of the patient's medical providers and a record of pertinent information relating to past clinical visits. For instance, the clinical attributes may include symptoms and/or test results associated with the patient 10. Here, symptoms and/or test results may indicate whether or not the patient 10 has established vascular complications. Financial attributes may include insurance coverage, salary, and/or education of the patient 10 for considering when prescribing a particular medication. For example, medications that are not covered by a patient's insurance plan may be difficult prescriptions for the patient to sustain, and therefore, alternative medications may need to be considered. The other relevant patient-state information may include, but is not limited to, a life expectancy of the patient, important comorbidities, established vascular complications, whether the patient's resources and support system are readily available or limited, and patient attitude. For example, the patient attitude may indicate whether the patient 10 is highly motivated and adherent with excellent self-care capacities, or whether the patient 10 is less motivated and non-adherent with poor self-care capabilities.

The BG history data 208b includes treatment doses and outcome attributes associated with each treatment dose administered by the patient. FIG. 2B shows the display 116, 146 prompting the user 40 with the option to manually input the BG history data 208b of the patient 10 upon selection of a "Manual" button or to download the BG history data 208b upon selection of a "Download" button. For instance, the patient's 10 smartphone 110b or tablet may communicate with the glucometer 124 and/or the insulin administration devices 123a, 123b via Bluetooth or other connection to download the BG history data 208b from the memory 114c of the glucometer 124, and transmit the downloaded BG history data 208b to the dosing controller 160 through the network 20. In other examples, the glucometer 124 may communicate directly with the dosing controller 160 to transmit the BG history data 208b from the memory 114c of the glucometer 124 to the dosing controller 160 through the network 20. FIG. 2C shows the display 116, 146 displaying the BG history data 208b as a chronological record of each insulin dose administered to the patient 10 and the outcome history indicating the BGnext occurring after each insulin dose. For example, the BGnext may correspond to a next scheduled BG measurement that occurs at a meal time after administering a meal bolus for a previous meal. In some examples, the BGnext associated with a breakfast bolus occurs at a pre-lunch time, the BGnext associated with a lunch bolus occurs at a pre-dinner time, and the BG next associated with a dinner bolus occurs at bedtime or at the next day's pre-breakfast time.

In some examples, the process 200 at block 208 requests the user 40 to enter SubQ information 208c for the patient 10, such as patient diabetes status, subcutaneous type ordered for the patient 10 (e.g., Basal/bolus and correction that is intended for patients on a consistent carbohydrate diet, total daily dosage (TDD), bolus insulin type (e.g., Novolog), basil insulin type (e.g., Lantus) and frequency of distribution (e.g., 1 dose per day, 2 doses per day, 3 doses per day, etc.), basil time, basal percentage of TDD, meal bolus percentage of TDD, daily meal bolus distribution (e.g., breakfast bolus, lunch bolus and dinner bolus), or any other relevant information. In some implementations, TDD is calculated in accordance with equation:

$$TDD = QuickTransitionConstant * M_{Trans} \tag{4A}$$

where QuickTransitionConstant is usually equal to 1000, and $M_{Trans}$ is the patient's multiplier at the time of initiation of the SubQ transition process. In other implementations, the TDD is calculated by a statistical correlation of TDD as a function of body weight. The following equation is the correlation used:

$$TDD = 0.5 * Weight \ (kg) \tag{4B}$$

In other implementations, the patient's total daily dose TDD is calculated in accordance with the following equation:

$$TDD = (BG_{Target} - K) * (M_{Trans}) * 24 \tag{4C}$$

where $M_{Trans}$ is the patient's multiplier at the time of initiation of a SubQ transition process.

In some implementations, the patient SubQ information 208c is prepopulated with default parameters, which may be adjusted or modified. In some examples, portions of the patient SubQ information 208c are prepopulated with previously entered patient subcutaneous information 208c. The process 200 may prompt the request to the user 40 to enter the SubQ information 208c on the display 116 of the patient device 110. In some implementations, the process 200 prompts the request on the display 116 for a custom start of new patients (FIG. 2B) undertaking the training program 300a or the treatment program 300b. The user 40 may enter SubQ information 208c including the patient's 10 correction factor CF (e.g., 1700) and target BG range for calculating the correction bolus CB using EQ. 2. As shown in FIG. 2B, the user 40 may enter an Insulin-to-Carbohydrate Ratio (ICR) for determining a recommended insulin dose based on a number of carbohydrates that the patient 10 consumes at an associated meal.

In some examples, the display 116, 146 may show the patient-state information 208a, the BG history data 208b, and/or the SubQ information 208c for an existing or returning patient 10. In these scenarios, the patient information 208a-c may be retrieved from the non-transitory memory 24, 114, 124 of the system 100 and displayed upon the display 116, 146 by entering the patient's 10 name and/or identification ID number (FIG. 2C). Once the process 200 obtains all the patient information 208a-c, the process 200 allows the user 40 to start the patient treatment program 300b. For example, FIGS. 2B and 2C allow the user 40 to start the patient treatment program 300b by selecting a "Treatment" button upon the display 116, 146.

The process 200 may allow the user 40 to determine a frequency and/or date-range of training data for use by the training program 300a (FIG. 3A). FIG. 2D shows an exemplary start mode selector 301 for the training program 300a that allows the user 40 to select one of an automatic start 303 of the training program 300a, an immediate start 305 of the training program 300a, or a clean re-start 307 of the training program 300a. The automatic start 303 may be a default setting for the training program 300a and may be configurable at an interval of Ndays. In some examples, the value for Ndays is equal to 60 days. However, the user 40 may desire an early or un-scheduled start of the training program 300a by selecting the immediate start 305. In some scenarios, selection of the clean re-start 307 re-initializes self-learning memories of the training program 300a (e.g., stored in non-transitory memory 24, 114, 124). The user 40 may select the clean re-start when changes to the training program 300a have been implemented or changes will occur at a known date. Accordingly, the user 40 may select a start of the data date-range via a calendar pull-down button, as shown on the display 116, 146 of FIG. 2D.

Referring to FIG. 3A, in some implementations, the training program 300a commences based on the selected user input to the start mode selector 301 of FIG. 2D. For instance, the training program 300a may start at block 302 in response to a selection of one of the automatic start 303, the immediate start 305, or the clean re-start 307 at the start mode selector 301 of FIG. 2D. The clean re-start 307 may be accompanied by a custom input start date and used when changes to the training program 300a result in previously obtained data to now be obsolete. FIG. 3A shows an overview of the training program 300a operating in the automatic start 303 with a time period of Ndays (e.g., 60 days). A process timer 306 may initiate to count the time period. The training program 300a is a periodic optimization process that may improve an insulin dose-advising program for treating diabetic patients. The training program 300a may apply to a SubQ meal bolus adjustment program 400a (FIG. 4A) and a SubQ basal adjustment program 400b (FIG. 4B). Each of the programs 400a, 400b may include decision trees for adjusting recommended insulin doses for meal bolus or basal, respectively.

At block 308, the training program 300a obtains the BG history data 208b associated with the patient 10 and provides the BG history data 208b as new training data at block 310. The new training data at block 310 also includes the patient's patient-state information 208a and the patient's SubQ information 208c. In some examples, only the BG history data 208b since the last cycle of the training program 300a is considered for use in the instant training program 300a. The new data may be added by default to the old data already stored in the training program 300a memory (non-transitory memory 24, 114, 124). If changes have been made to the training program 300a, however, the user 40 may override the default and direct a re-initialization of the memories in the training program 300a via selection of the clean re-start 307 in the start mode selector 301 of FIG. 2D.

The training program processes the new training data at block 310 to obtain counts and calculate probabilities in the manner of tree-training based on the patient's patient-state information 208a, BG history data 208b, and/or SubQ information 208c. The training program 300a may obtain the new training data at block 310 chronologically one dose adjustment (e.g., bolus or basal) at a time. The BG history data 208b may include a calculation of an insulin dose administered to the patient 10 and the outcome data associated with the insulin dose, obtained at a time when the next scheduled blood glucose measurement BGnext shows the result of the administered insulin dose.

At block 312, each patient-state attribute PA, PA1-PAj of the patient's patient-state information 208a is provided to block 314. A tree connector for each patient-state attribute PA may extend from block 312 for input in block 314. In some examples, block 314 corresponds to a parent box associated with all the patient-state attributes PA of the patient 10 and collectively includes one or more child boxes each pertaining to respective ones of the patient-state attributes PA. The training program 300a, at block 314, may increment counts for each patient-state attribute during each dose adjustment, and calculate probabilities for each patient-state attribute. Accordingly, the training program 300a may designate an appropriate box for each patient-state attribute of the patient 10 one dose adjustment at a time. Advantageously, the training program 300a builds a classifier for a patient population that may be used to predict group attributes of new cases from the domain knowledge base based on values of other attributes. While FIG. 3A shows the training program 300a using the decision tree for classifying attributes, the training program 300a may also use other classification methods such as IF-Then Rule Induction, Bayesian Classifiers, Naïve Baysian Classifiers, Iterative Dichotomiser 3 (ID3) algorithms, K Nearest Neighbor, and Neural Networks.

The training program 300a, at block 316, processes the patient-state information 208a, the BG history data 208b, and the SubQ information 208c to calculate the adjusted insulin dose for the patient 10, and subsequently recommend the adjusted insulin dose to the patient 10. For example, the dosing controller 160 may transmit the adjusted insulin dose to the patient computing device 110. In some examples, the dosing controller 160 transmits the adjusted insulin dose calculated at block 316 to the administration device 123a, 123b and the doser 223a, 223b administers the insulin to the patient 10. Block 316 may include each adjusted insulin dose TA, TA1-TAj during the time period of Ndays selected for the training program. The training program 300a, at block 316, may increment counts for each adjusted insulin dose, and calculate probabilities for each of the adjusted insulin doses.

Referring to block 318, the training program 300a obtains an outcome attribute associated with the adjusted insulin dose calculated and administered at block 316. Block 318 may include outcome attributes OA, OA1-OAi associated with each of the adjusted insulin doses TA, TA1-TAj administered by the patient 10 at block 316. The training program 300a, at block 318, may increment counts for each outcome attribute, and calculate probabilities for each of the outcome attributes.

The outcome attribute may include the BGnext occurring a sufficient period of time (e.g., four to six hours) after the adjusted dose is administered by the patient. In some examples, when the adjusted dose corresponds to a meal bolus dose, the training program 300a calculates an evaluation or a "grade" on the adjusted dose administered by the patient 10 at block 316. For example, the BGnext may be further processed into another outcome attribute, BG Percent Error (Err %), calculated in accordance with the following equation:

$$Err\% = ABS[(BGnext - BG_{TC})/BG_{TC}] \qquad (5)$$

where $BG_{TC}$ is the Target Center of the BG Target Range $BG_{TR}$ obtained from the SubQ information 208c.

Subsequently, at block 318, the training program 300a may average the BGnext (MeanBGnext) and the Err % (MeanErr %) for each adjusted insulin dose and store the values in a child box contained by a parent box corresponding to the adjusted meal bolus dose. Accordingly, the training program 300a calculates the evaluation or "grade" on each adjusted meal bolus dose based on one or more outcome attributes associated with the adjusted meal bolus dose. Here, adjusted meal bolus doses of insulin resulting in favorable outcome attributes are assigned higher "grades" than those resulting in less favorable outcome attributes. Thus, the training program 300a may identify a best or optimum treatment dose of insulin (e.g., best or optimum meal bolus dose) from one of the adjusted meal bolus doses of insulin administered by the patient that yields the most favorable outcome attribute.

In some examples, when the adjusted insulin dose calculated and administered by the patient 10 at block 316 corresponds to an adjusted basal dose, the outcome attribute at block 318 may include a next scheduled breakfast BG measurement (BGbreakfastNext) occurring after the adjusted basal dose is administered at block 316. Here, the BGbreakfastNext is obtained after the patient 10 has fasted during sleep to accurately show how well the adjusted basal dose controlled the patient's blood glucose levels. In some examples, when the adjusted dose corresponds to the basal dose, the training program 300a calculates an evaluation or a "grade" on the adjusted dose administered by the patient 10 at block 316. For example, the BGbreakfastNext may be further processed into another outcome attribute, BGbreakfast Percent Error (BrkErr %), calculated in accordance with the following equation:

$$BrkErr\%=ABS[(BGBreakfastNext-BG_{TC})/BG_{TC}] \quad (6)$$

Subsequently, at block 318, the training program 300a may average the BrkErr % (MeanBrkErr %) for each adjusted insulin dose and store the values in a child box contained by a parent box associated with the adjusted dose corresponding to the adjusted basal dose. Accordingly, the training program 300a calculates the evaluation or "grade" on each adjusted basal dose based on one or more outcome attributes associated with the adjusted basal dose. Here, adjusted basal doses of insulin resulting in favorable outcome attributes are assigned higher "grades" than those resulting in less favorable outcome attributes. Thus, the training program 300a may identify a best or optimum treatment dose of insulin (e.g., best or optimum basal dose) from one of the adjusted basal doses of insulin administered by the patient that yields the most favorable outcome attribute.

The training program 300a may proceed back to block 302 and obtain the BG history data 208b at block 308 for another dose-adjustment history. Upon completing the training program 300a for each insulin dose to be adjusted, the training program 300a stops the iterative process of incrementing the counts and calculating the probabilities within the non-transitory memory 24, 114, 124 at each of blocks 314, 316, 318. The training program 300a may build the decision tree for a patient population based on the patient-state information 208a, BG history data 208b, and the SubQ information 208c for each patient of the patient population. Accordingly, the decision tree may be retrieved from the non-transitory memory 24, 114, 124 for use by the patient treatment program 300b to allow the user 40 (e.g., physician or medical professional) to prescribe a personalized patient treatment therapy for a patient 10.

Referring to FIG. 3B, in some implementations, the treatment program 300b uses the training data contained in the decision tree processed by the training program 300a for determining an optimum insulin dose and recommending the optimum insulin dose to a patient in treatment. The treatment program 300b commences at block 330 with a new patient or a returning patient. At block 330, the treatment program obtains the patient information associated with the new or returning patient. The patient information may include patient-state information 208a, BG history data 208b, and SubQ information 208c.

At block 312, each patient-state attribute PA, PA1-PAj of the patient's patient-state information 208a is provided to block 314. A tree connector for each patient-state attribute PA may extend from block 312 for input in block 314. In some examples, block 314 corresponds to a parent box associated with all the patient-state attributes PA of the patient 10 and collectively includes one or more child boxes each pertaining to respective ones of the patient-state attributes PA. Accordingly, the treatment program 300b may assign each patient-state attribute of the patient 10 into a corresponding box associated with the training program 300a of FIG. 3A. The treatment program 300b, however, does not increment counts or calculate probabilities for the patient-state attributes associated with the patient 10 being treated.

At block 336, the treatment program 300b processes the patient-state information 208a, the BG history data 208b, and the SubQ information 208c to determine a recommended insulin dose RA1, RA2-RAj for the patient 10. However, rather than providing the recommended insulin dose for the patient 10 to administer, the treatment program 300b, at block 338, compares the recommended insulin dose with the adjusted insulin doses TA, TA1-TAj and the associated outcome attributes OA, OA1-OAi obtained from the training program 300a. Here, the adjusted insulin doses TA, TA1-TAj calculated in block 316 of the training program 300a and the associated outcome attributes OA, OA1-OAi obtained from blocks 318 and 338, respectively, of the training program 300a, may only correspond to patients of the patient population that have the same diagnosis and similar patient-state attributes as the patient 10 being treated. Accordingly, the treatment program 300b, at block 340, may determine (e.g., predict) an optimum insulin dose for the patient 10 that will yield a most favorable outcome attribute based on the comparison with the adjusted insulin doses and associated outcome attributes obtained from the training program 300a. In some examples, the optimum insulin dose for the patient 10 corresponds to the best treatment dose of insulin identified at block 318 of the patient training program 300a for one or more patients of the patient population that have similar patient-state attributes as the patient 10 being treated. Block 340 may provide the optimum insulin dose for the patient 10 to block 336 to replace the insulin dose previously recommended. The reporting module 80 of the system 100 may recommend the optimum insulin to the patient 10 by transmitting the optimum insulin dose to the patient computing device 110 for the patient 10 to view upon the display 116, transmitting an email containing the optimum insulin dose to the patient 10, and/or printing the optimum insulin dose in a report for the patient 10. In some examples, the dosing controller 160 executing the treatment program 300b may transmit the optimum insulin dose to the administration device 123 (e.g., pump 123a or smart pen 123b) so that the administration computing device 112d, 112e may instruct the doser 223a, 223b to administer the optimum insulin dose to the patient 10.

Figure 3C:
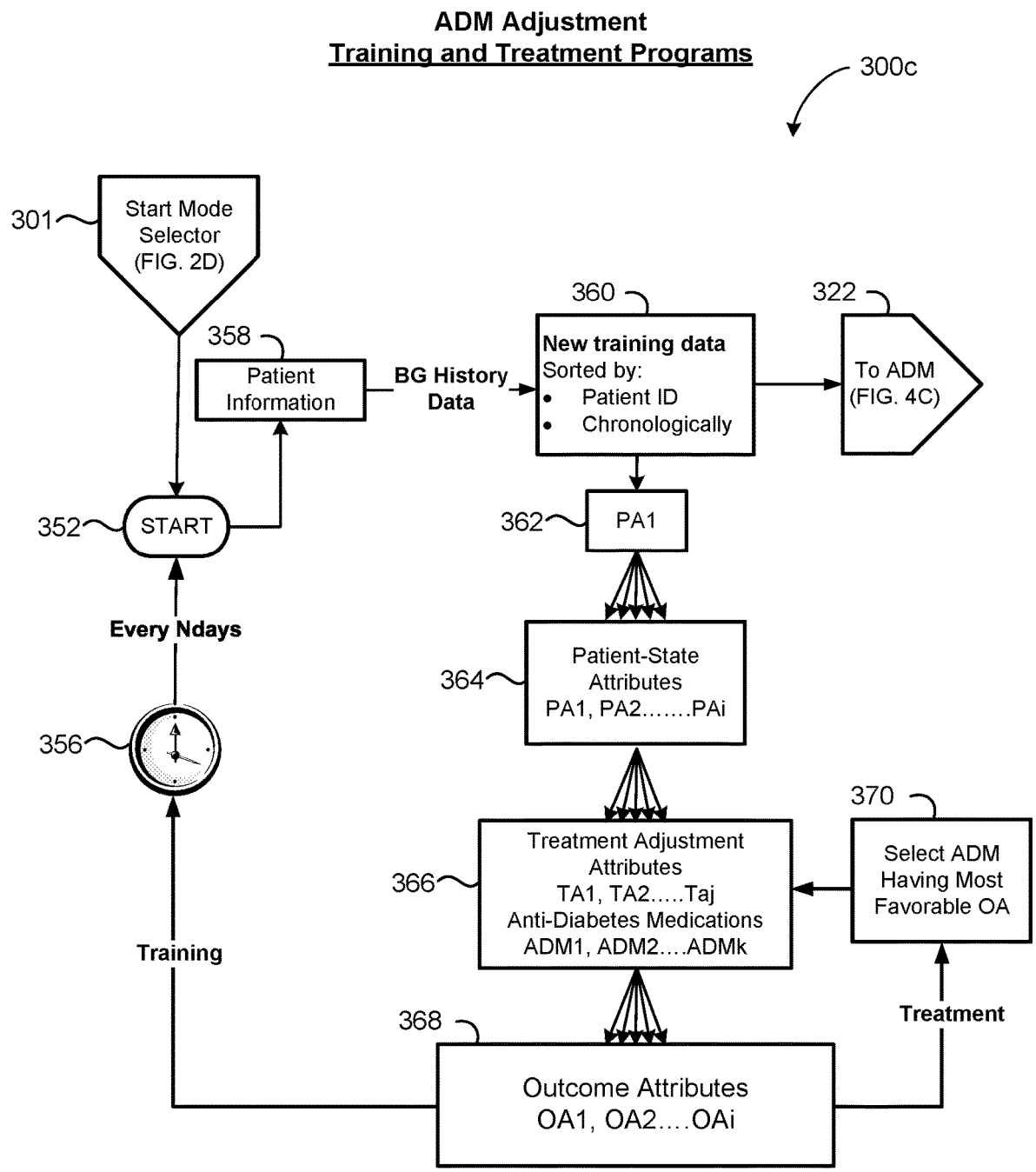
FIG. 3C is a schematic view of an exemplary anti-diabetes program for prescribing Anti-Diabetes Medication dose-combinations to a patient.

Referring to FIG. 3C, in some implementations, an anti-diabetes program 300c prescribes ADM dose-combinations to a patient 10 for delaying, and in some instances eliminating, the progression of diabetes. FIG. 3C provides an overview combining the training and treatment programs 300a, 300b, respectively, for adjusting ADMs. Accordingly, the present disclosure may refer to the program 300c as an anti-diabetes program or an ADM program. The program 300c may operate in a training mode or in a treatment mode. The training mode of the program 300c includes a periodic optimization process that may improve a non-insulin dose-advising program for treating patients with a high probability of becoming diabetic or for treating patients diagnosed with Type 2 diabetes mellitus (DM2). The anti-diabetes program may apply to an ADM adjustment program 400c (FIG. 4C) that may include decision tress for adjusting recommended doses of one or more ADMs. The training mode of the anti-diabetes program 300c may start in response to a selection of one of the automatic start 303, the immediate start 305, or the clean re-start 307 at the start mode selector 301 of FIG. 2D. The clean re-start 307 may be accompanied by a custom input start date and used when changes to the anti-diabetes program 300c result in previously obtained data to now be obsolete. FIG. 3C shows the anti-diabetes program 300c operating in the automatic start 303 with a time period of Ndays (e.g., 60 days). A process timer 356 may initiate to count the time period.

At block 358, the training mode of the program 300c obtains the BG history data 208b associated with the patient 10 and provides the BG history data 208b as new training data at block 360. The new training data at block 360 may also include the patient's patient-state information 208a. In some examples, only the BG history data 208b since the last cycle of the training mode of the program 300a is considered for use in the instant training mode cycle. The new data may be added by default to the old data already stored in the training program 300a memory (non-transitory memory 24, 114, 124). If changes have been made to the anti-diabetes program 300c, however, the user 40 may override the default and direct a re-initialization of the memories in the program 300c via selection of the clean re-start 307 in the start mode selector 301 of FIG. 2D.

During the training mode, the anti-diabetes program 300c processes the new training data at block 360 to obtain counts and calculate probabilities in the manner of tree-training based on the patient's patient-state information 208a and the BG history data 208b. The training mode of the program 300c may obtain the new training data at block 360 chronologically one ADM dose adjustment at a time. The BG history data 208b may include a calculation of one or more ADM dose-combinations administered by the patient 10 and the outcome data corresponding to an A1c level associated with the one or more ADM doses administered by the patient 10. Additionally or alternatively, the outcome data may include a next scheduled blood glucose measurement BGnext occurring a sufficient time after the patient 10 administers the ADM dose-combination, and thereby showing the glycemic result of the ADM dose-combination.

At block 362, each patient-state attribute PA, PA1-PAj of the patient's patient-state information 208a is provided to block 364. A tree connector for each patient-state attribute PA may extend from block 362 for input in block 364. In some examples, block 364 corresponds to a parent box associated with all the patient-state attributes PA of the patient 10 and collectively includes one or more child boxes each pertaining to respective ones of the patient-state attributes PA. During the training mode, the anti-diabetes program 300c, at block 364, may increment counts for each patient-state attribute during each dose adjustment, and calculate probabilities for each patient-state attribute. Accordingly, the training mode of the program 300c may designate an appropriate box for each patient-state attribute of the patient 10 one dose adjustment at a time. Advantageously, the training mode of the program 300c builds a classifier for a patient population that may be used to predict group attributes of new cases from the domain knowledge base based on values of other attributes. While FIG. 3C shows the anti-diabetes program 300c using the decision tree for classifying attributes, the anti-diabetes program 300c may also use other classification methods such as IF-Then Rule Induction, Bayesian Classifiers, Naïve Baysian Classifiers, Iterative Dichotomiser 3 (ID3) algorithms, K Nearest Neighbor, and Neural Networks.

The anti-diabetes program 300c, at block 366, processes the patient-state information 208a, the BG history data 208b, and the SubQ information 208c to calculate the adjusted ADM dose-combination for the patient 10 and subsequently recommends the adjusted ADM dose-combination to the patient 10. Block 366 may include each ADM dose-combination TA, TA1-TAj and corresponding ADMs ADM1, ADM2-ADMk during the time period of Ndays selected for the training mode of the anti-diabetes program 300c. The anti-diabetes program 300c, at block 368, may increment counts for each ADM dose-combination, and calculate probabilities for each of the ADM dose-combinations during the training mode. During the treatment mode, however, block 366 does not increment counts or calculate probabilities.

Referring to block 368, the program 300c obtains an outcome attribute associated with the ADM dose-combinations calculated and administered at block 366. Block 368 may include outcome attributes OA, OA1-OAi associated with each of the ADM dose-combination TA, TA1-TAj administered by the patient 10 at block 366. The training mode of the anti-diabetes program 300c, at block 368, may increment counts for each outcome attribute, and calculate probabilities for each of the outcome attributes. During the treatment mode, however, the anti-diabetes program 300c does not increment counts or calculate probabilities at block 368.

The outcome attribute may include a next scheduled A1c level (A1cNext) occurring after the ADM dose-combination is administered by the patient. In some scenarios, the A1cNext is obtained by the anti-diabetes program 300c within two to three months after the ADM dose-combination is administered by the patient 10. In some examples, during the training mode, the anti-diabetes program 300c calculates an evaluation or a "grade" on the ADM dose-combination administered by the patient 10 at block 366. For example, the anti-diabetes program 300c may average the A1cNext (MeanA1cNext) for each of the ADM dose-combination administered by the patient 10 and store the values in a child box contained by a parent box associated with ADM dose-combinations.

The training mode of the anti-diabetes program 300c may proceed back to block 352 and obtain the BG history data 208b at block 358 for another dose-adjustment history. Upon adjusting each ADM dose during the designated period of time Ndays, the training mode ends and the anti-diabetes program 300c stops the iterative process of incrementing the counts and calculating the probabilities within the non-transitory memory 24, 114, 124 at each of blocks 364, 366, 368. As with the training program 300a of FIG. 3A, the anti-diabetes program 300c may process a decision tree during the training mode for a patient population based on the patient-state information 208a and the BG history data 208b for each patient of the patient population.

During the treatment mode, the anti-diabetes program 300c uses the training data contained in the decision tree processed during the training mode for determining an optimum ADM dose-combination and recommending the optimum ADM dose-combination to a patient 10 in treatment. The treatment mode may commence at block 360 by obtaining patient-state information 208a and BG history data 208b associated with a new or returning patient 10. As with the training mode, the treatment mode of the anti-diabetes program 300c may assign each patient-state attribute of the new or returning patient 10 into a corresponding box at block 364. However, the treatment mode does not increment counts or calculate probabilities for the patient-state attributes associated with the patient 10 being treated. At block 366, the anti-diabetes program 300c processes the patient-state information 208a and the BG history data 208b and calculates a recommended ADM dose-combination for the patient 10. Rather than providing the recommended ADM dose-combination for the patient 10 to administer, the treatment mode of the program 300c, at block 368, compares the recommended ADM dose-combination with the adjusted ADM dose-combinations TA, TA1-TAj and associated outcome attributes OA, OA1, OAi obtained from the training data during the training mode. Here, the anti-diabetes program 300c may compare the recommended ADM dose-combination with the adjusted ADM dose-combinations TA, TA1-TAj and associated outcome attributes OA, OA1, OAi that only correspond to patients of the patient population that have the same diagnosis and similar patient-state attributes as the patient 10 being treated. According, at block 370, the treatment mode of the program 300c may determine an optimum ADM (insulin or non-insulin) dose-combination for the patient 10 that that will yield a most favorable outcome attribute based on the adjusted ADM dose-combinations and associated outcome attributes obtained from the training data. Block 370 may provide the optimum ADM dose-combination to block 366 to replace the ADM dose-combination previously recommended. The reporting module 80 of the system 100 may recommend the optimum ADM dose-combination to the patient 10 by transmitting the optimum ADM dose-combination to the patient computing device 110 for the patient 10 to view upon the display 116, transmitting an email containing the optimum ADM dose-combination to the patient 10, and/or printing the optimum ADM dose-combination in a report for the patient 10.

Figure 4A:
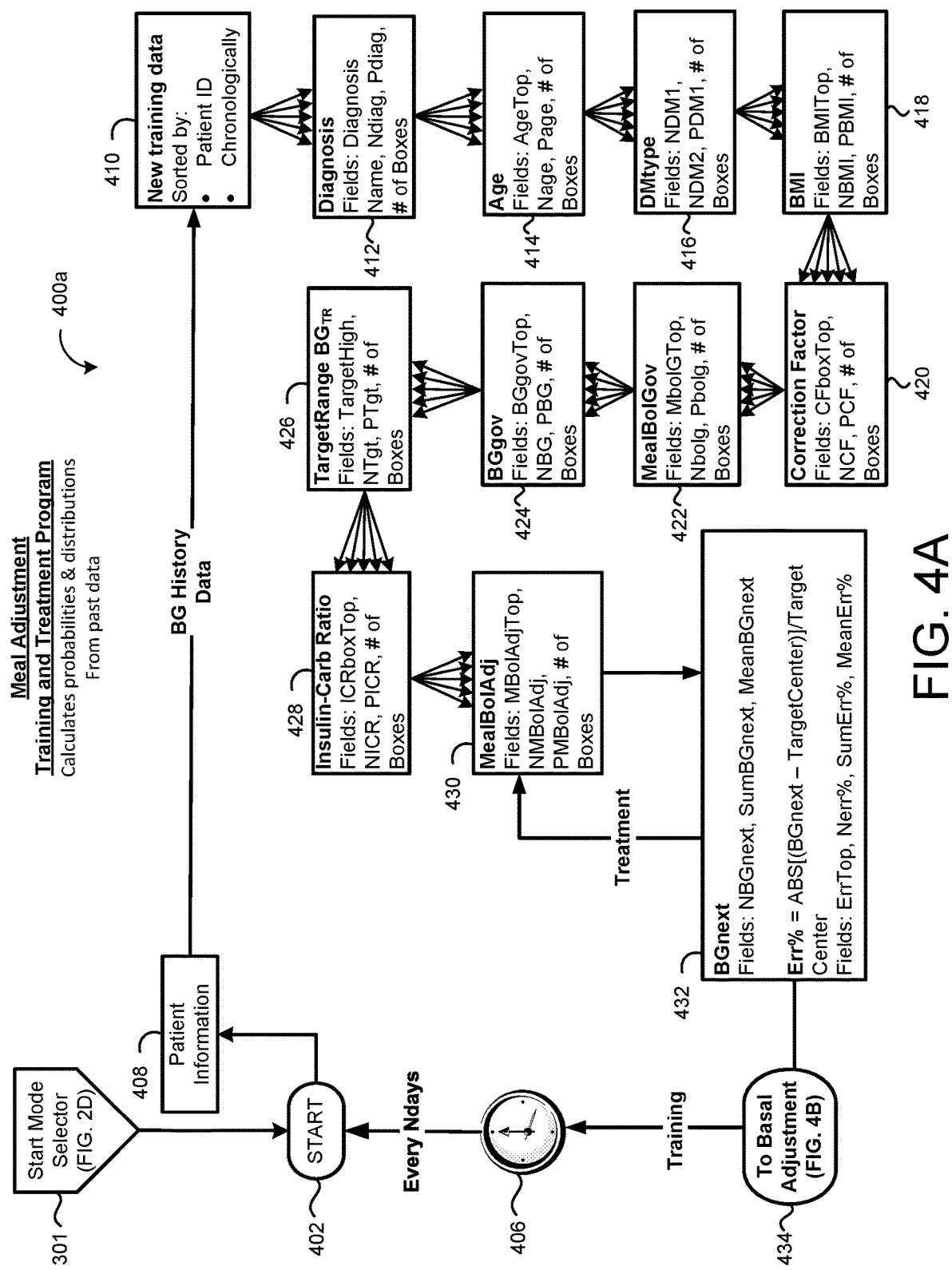
FIG. 4A is a schematic view of an exemplary subcutaneous meal bolus adjustment program.
Figure 4B:
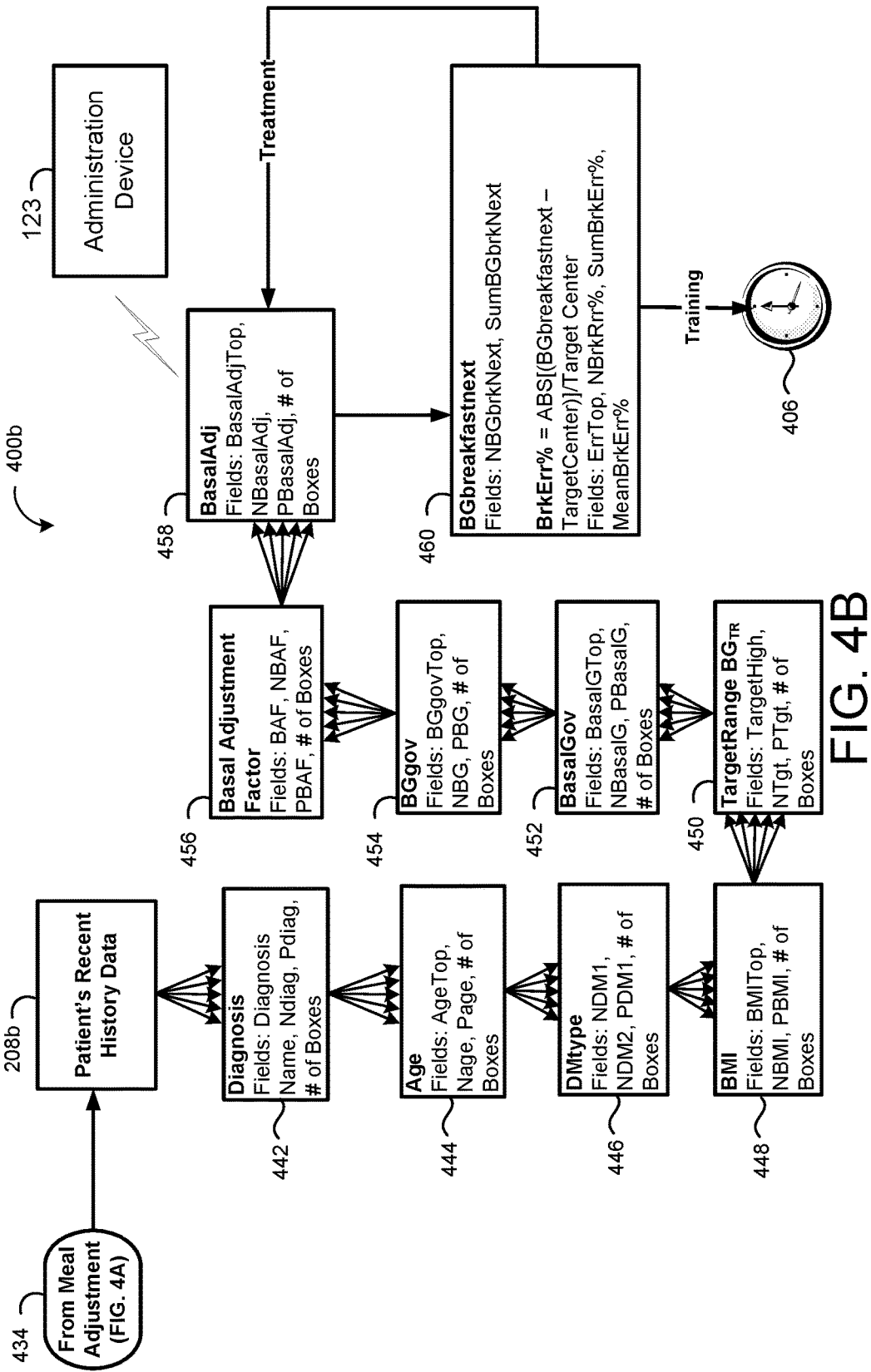
FIG. 4B is a schematic view of an exemplary subcutaneous basal adjustment program.

Referring to FIG. 4A, in some implementations, a SubQ meal bolus adjustment program 400a may operate in a training mode associated with the training program 300a (FIG. 3A) and a treatment mode associated with the treatment program 300b (FIG. 3B). FIG. 4A provides details of training and treatment for adjusting meal boluses. The SubQ meal bolus adjustment program 400a may execute on a computing device, such as service provider data processing hardware 130, 160, a cloud resource, or some other computing device 112, 132, 142. As with the training program 300a, the training mode of the SubQ meal bolus adjustment program 400a may start at block 402 in response to a selection of one of the automatic start 303, the immediate start 305, or the clean re-start 307 at the start mode selector 301 of FIG. 2D. The clean re-start 307 may be accompanied by a custom input start date and used when changes to the training program 300a result in previously obtained data to now be obsolete. FIG. 4A shows the training mode of program 400a operating in the automatic start 303 with a time period of Ndays (e.g., 60 days). A process timer 406 may initiate to count the time period. The training mode is a periodic optimization process that may improve the meal bolus dose recommendations determined by the SubQ meal bolus adjustment program 400a.

At block 408, the treatment mode of the SubQ meal bolus adjustment program 400a obtains patient information including the BG history data 208b associated with the patient 10 and provides the BG history data 208b as new training data at block 410. The new training data at block 410 also includes the patient's patient-state information 208a and the patient's SubQ information 208c. The SubQ meal bolus adjustment program 400a may obtain the new training data at block 410 chronologically one meal bolus dose adjustment at a time. The BG history data 208b may include a calculation of an insulin dose (e.g., meal bolus) administered by the patient 10 and the outcome data associated with the insulin dose, obtained at a time when the next scheduled blood glucose measurement BGnext shows the result of the administered insulin dose.

The SubQ meal bolus adjustment program 400a includes blocks 410-428 for processing associated attributes obtained from patient's patient-state information 208a, BG history data 208b, and/or SubQ information 208c. Each block 410-428 may obtain a count and calculate a probability for the associated attributed in a manner of tree-training based on the patient's patient-state information 208a, BG history data 208b, and/or SubQ information 208c obtained from the training data at block 410. Each block 410-428 may include one or more child attribute boxes associated with a parent attribute box. For each attribute, the blocks 410-428 may determine an appropriate box and increment the count (N) by one and calculate a likelihood or probability (P) in each box in accordance with the following equation:

$$P = (N \text{ in child box})/(N \text{ in parent box}) \qquad (7)$$

where the child box corresponds to a current attribute.

At block 412, a patient's diagnosis attribute obtained from the patient-state information 208a is compared to child boxes associated with the diagnosis attribute. The child box associated with the patient's diagnosis is then selected and the diagnosis count Ndiag is incremented by one and the diagnosis probability Pdiag is calculated using Eq. 7.

At block 414, a patient's age attribute obtained from the patient-state information 208a is compared to child boxes associated with the age attribute. Each child box may correspond to an age in years or an associated range of ages in years. The child box associated with the patient's age is then selected and the age count Nage is incremented by one and the age probability Page is calculated using Eq. 7. In some examples, the box associated with the patient's age is selected by iteratively comparing the patient's age to an upper bound of the age attribute (AgeTop) starting from the youngest age, and using a logic phrase in accordance with the following expression: IF Age<AgeTop THEN Nage=Nage+1.

At block 416, a patient's diabetic type DMtype obtained from the patient-state information 208a is compared to child boxes associated with the DMtype attribute. The DMtype attribute at block 416 may include three child boxes: one box for DM1, one box for DM2, and one box for "not recorded." The child box associated with the patient's DMType is then selected and the DMType count NDM1 or NDM2 is incremented by one and the probability PDM1 or PDM2 is calculated using Eq. 7.

At block 418, the patient's body mass index (BMI) is determined by the weight and height of the patient obtained from the patient-state information 208a and compared to child boxes associated with the BMI attribute. Each child box may correspond to a BMI value or an associated range of BMI values. The child box associated with the patient's BMI is then selected and the BMI count NBMI is incremented by one and the BMI probability PBMI is calculated using Eq. 7. In some examples, the box associated with the patient's BMI is selected by iteratively comparing the patient's BMI to an upper bound of the BMI attribute (BMITop) starting from the lowest BMI, and using a logic phrase in accordance with the following expression: IF BMI<BMITop THEN NBMI=NBMI+1.

At block 420, the patient's correction factor (CF) obtained from the SubQ information 208c is compared to child boxes associated with the CF attribute. Each child box may correspond to a CF value or an associated range of CF values. The child box associated with the patient's CF is then selected and the CF count NCF is incremented by one and the CF probability PCF is calculated using Eq. 7. In some examples, the box associated with the patient's CF is selected by iteratively comparing the patient's CF to an upper bound of the CF attribute (CFTop) starting from the lowest CF, and using a logic phrase in accordance with the following expression: IF CF<CFTop THEN NCF=NCF+1.

At block 422, the SubQ meal bolus adjustment program 400a chronologically adjusts the meal bolus insulin dose one dose adjustment at a time. The meal bolus being adjusted is referred to as a Governing Meal Bolus (MealBolusGov). The MealBolusGov may be obtained from the BG history data 208b and compared to child boxes associated with the MealBolusGov attribute. Each child box may correspond to a MealBolusGov value or an associated range of MealBolusGov values. The program 400a selects the child box associated with the patient's MealBolusGov, increments a count Nbolg by one, and calculates the MealBolusGov probability Pbolg using Eq. 7. In some examples, the box associated with the patient's MealBolusGov is selected by iteratively comparing the patient's MealBolusGov to an upper bound of the MealBolusGov attribute (MbolGTop) starting from the lowest MealBolusGov, and using a logic phrase in accordance with the following expression: IF MealBolusGov<MbolGTop THEN Nbolg=Nbolg+1.

At block 424, the program 400a obtains the patient's next scheduled blood glucose measurement (BGgov) after the patient 10 administers the MealBolusGov from the BG history data 208b and compares the BGgov to child boxes associated with the BGgov attribute. Each child box may correspond to a BGgov value or an associated range of BGgov values. The program 400a selects the child box associated with the patient's BGgov, increments a count NBG by one, and calculates the BGgov probability PBG using Eq. 7. In some examples, the box associated with the patient's BGgov is selected by iteratively comparing the patient's BGgov to an upper bound of the BGgov attribute (BGgovTop) starting from the lowest BGgov, and using a logic phrase in accordance with the following expression: IF BGgov<BGgov Top THEN NBG=NBG+1.

At block 426, the SubQ meal bolus adjustment program 400a obtains the patient's blood glucose target range $BG_{TR}$ from the SubQ information 208c and compares the $BG_{TR}$ to child boxes associated with the $BG_{TR}$ attribute. The program 400a selects the child box associated with the patient's $BG_{TR}$, increments a count NTgt by one, and calculates the $BG_{TR}$ probability PTgt using Eq. 7. In some examples, the box associated with the patient's $BG_{TR}$ is selected by iteratively comparing the patient's $BG_{TR}$ to an upper bound of the $BG_{TR}$ attribute (TargetHigh) starting from the greatest $BG_{TR}$, and using a logic phrase in accordance with the following expression: IF $BG_{TR}$<TargetHigh THEN NTgt=NTgt+1.

The SubQ meal bolus adjustment program 400a, at block 428, obtains the patient's insulin-carbohydrate ratio (ICR) from the SubQ information 208c and compares the ICR to child boxes associated with the ICR attribute. The program 400a selects the child box associated with the patient's ICR, increments a count NICR by one, and calculates the ICR probability PICR using Eq. 7. In some examples, the box associated with the patient's ICR is selected by iteratively comparing the patient's ICR to an upper bound of the ICR attribute (ICRboxTop) starting from the lowest ICR, and using a logic phrase in accordance with the following expression: IF ICR<ICRboxTop THEN NICR=NICR+1.

After the SubQ meal bolus adjustment program 400a processes each of the patient's attributes within blocks 410-428 during the training mode, the program 400a proceeds to block 430 and obtains an Adjusted Meal Bolus (MealBolAdj). In some examples, the MealBolAdj corresponds to the next meal bolus occurring after the MealBolGov of block 422. For instance, if the MealBolGov includes a breakfast meal bolus, the MealBolAdj will correspond to a lunch meal bolus on the same day. In other examples, the MealBolAdj corresponds to the same meal bolus as the MealBolGov, but on the next day. For instance, if the MealBolGov includes a dinner meal bolus, the MealBolAdj will correspond to the dinner meal bolus occurring on the next day. During the training mode, the program 400a compares the MealBolAdj to child boxes associated with the MealBolAdj attribute. Each child box may correspond to a MealBolAdj value or an associated range of MealBolAdj values. The program 400a selects the child box associated with the patient's MealBolAdj, increments a count NMbolAdj by one, and calculates the MealBolAdj probability PMBolAdj using Eq. 7. In some examples, the box associated with the patient's MealBolAdj is selected by iteratively comparing the patient's MealBolAdj to an upper bound of the MealBolAdj attribute (MbolAdjTop) starting from the lowest MealBolAdj, and using a logic phrase in accordance with the following expression: IF MealBolAdj<MbolAdjTop THEN NMbolAdj=NMbolAdj+1. The SubQ meal bolus adjustment program 400a may recommend an adjusted insulin dose associated with the MealBolAdj to the patient 10 for the patient 10 to administer. For example, the dosing controller 160 may transmit the MealBolAdj to the patient computing device 110 or to the patient's administration device 123a, 123b.

Subsequent to processing the patient's MealBolAdj at block 430, the SubQ meal bolus adjustment program 400a, at block 432, obtains one or more outcome attributes associated with the patient's MealBolAdj. The outcome attribute may include the BGnext that occurs a sufficient period of time (e.g., four to six hours) after the adjusted dose is administered by the patient 10. The program 400a may increment a count for the BGnext (NBGnext) by one. Additionally, during the training mode, the program 400a may calculate an evaluation or a "grade" on the MealBolAdj administered by the patient 10 based on the BGnext. For example, the program 400a may process the BGnext to calculate the BG Percent Error (Err %) using Eq. 5 and increment a count for the Err % (Nerr %) by one. The SubQ meal bolus adjustment program 400a may also calculate a sum for each BGnext (SumBGnext) and each Err % (SumErr %) for each MealBolAdj, and then average the BGnext (MeanBGnext) and the Err % (MeanErr %) for each MealBolAdj. The values for the SumBGnext, the SumErr %, the MeanBGnext, and the MeanErr % may be stored in a child box contained by a parent box corresponding to the MealBolAdj. Accordingly, the meal bolus adjustment program 400a calculates the evaluation or "grade" on each MealBolAdj based on one or more outcome attributes associated with the MealBolAdj. Here, MealBolAdj values yielding favorable outcome attributes are assigned higher "grades" than those resulting in less favorable outcome attributes. Thus, the program 400a may identify a best or optimum treatment dose of insulin (e.g., best or optimum MealBolAdj) from one of the MealBolAdj doses of insulin administered by the patient 10 that yields the most favorable outcome attribute.

Upon completing the training mode for each MealBolAdj, the SubQ meal bolus adjustment program 400a stops the iterative process of incrementing the counts and calculating the probabilities within the non-transitory memory 24, 114, 124 at each of blocks 410-430. Thus, as with the training program 300a (FIG. 3A), the training mode of the SubQ meal bolus adjustment program 400a builds a decision tree for a patient population based on the patient-state information 208a, BG history data 208b, and the SubQ information 208c for each patient of the patient population. Thereafter, the treatment mode of the SubQ meal bolus adjustment program 400a may retrieve the decision tree from the non-transitory memory 24, 114, 124 to allow the user 40 (e.g., physical or medical professional) to prescribe an optimum MealBolAdj that is personalized for a patient 10 being treated.

During the treatment mode, the SubQ meal bolus adjustment program 400a uses the training data contained in the decision tree processed during the training mode for determining an optimum MealBolAdj and recommending the optimum MealBolAdj to a patient 10 in treatment. The treatment mode may commence at block 410 by obtaining patient-state information 208a, BG history data 208b, and SubQ information 208c associated with a new or returning patient 10 being treated. As with the training mode, the treatment mode of the SubQ meal bolus adjustment process 400a may assign each of the new or returning patient's attributes into corresponding boxes at each of blocks 410-428. However, the treatment mode does not increment counts or calculate probabilities for the boxes associated with the patient's 10 attributes. At block 430, the program 400a selects the optimum insulin dose for the MealBolAdj (e.g., optimum MealBolAdj) for the new or returning patient 10 based on the MealBolAdj from the training mode that is associated with a lowest MeanErr %. Thus, the treatment mode of the program 400a selects the optimum MealBolAdj that will yield a most favorable outcome attribute (e.g., lowest MeanErr %) based on the training data of the training mode. Block 430 may use the reporting module 80 of the system 100 to recommend the optimum MealBolAdj to the patient 10 being treated through transmission to the patient computing device 110 for the patient 10 to view upon the display, through transmission of an email containing the optimum MealBolAdj, and/or printing the optimum MealBolAdj in a report for the patient 10. In some examples, the dosing controller 160 executing the SubQ meal bolus adjustment program 400a at block 430 may transmit the optimum MealBolAdj to the administration device 123 (e.g., pump 123a or smart pen 123b) so that the administration computing device 112d, 112e may instruct the doser 223a, 223b to administer the optimum insulin dose to the patient 10.

Referring to FIG. 4B, in some implementations, a SubQ basal adjustment program 400b may operate in a training mode associated with the training program 300a (FIG. 3A) and a treatment mode associated with the treatment program 300b (FIG. 3B). The training mode may commence after the training mode of the SubQ meal bolus adjustment program 400a (FIG. 4A) completes at block 434 of FIG. 4A. The SubQ basal adjustment program 400b uses the new training data (e.g., patient-state information 208a, BG history data 208b, and SubQ information 208c) from block 410 of the SubQ meal bolus adjustment program 400a which is sorted by patient ID and chronologically one basal dose adjustment at a time. Accordingly, the training mode of the SubQ basal adjustment program 400b completes the process of obtaining the BG history data 208b associated with basal insulin dose adjustments and outcome attributes associated therewith. Thus, each basal insulin dose adjustment and the associated one or more outcome attributes may include a respective date-stamped event.

The training mode of the SubQ basal adjustment program 400b includes blocks 442-456 for processing associated attributes obtained from patient's patient-state information 208a, BG history data 208b, and/or SubQ information 208c. Similar to the training mode of the SubQ meal bolus adjustment program 400a (FIG. 4A), each block 442-456 of the SubQ basal adjustment program 400b during the training mode may obtain a count and calculate a probability for the associated attributed in a manner of tree-training based on the patient's patient-state information 208a, BG history data 208b, and/or SubQ information 208c obtained from the training data at block 410. Each block 442-456 may include one or more child attribute boxes associated with a parent attribute box. For each attribute, the blocks 442-456 may determine an appropriate box and increment the count (N) by one and calculate a likelihood or probability (P) in each box using Eq. 7.

At block 442-448, the training mode of the SubQ basal adjustment program 400b selects the child box, increments the count N by one and calculates the probability P within each box for each of the attributes associated with the patient's diagnosis, age, diabetic type DMtype, and body mass index (BMI) in the same manner as discussed above with reference to blocks 412-418 of the SubQ meal bolus adjustment program 400a of FIG. 4A. At block 450, the training mode of the SubQ basal adjustment program 400b obtains the patient's blood glucose target range $BG_{TR}$ from the SubQ information 208c and compares the patient's $BG_{TR}$ to child boxes associated with the $BG_{TR}$ attribute at block 450. Similar to block 426 of the SubQ meal bolus adjustment program 400a (FIG. 4A), the training mode of the SubQ basal adjustment program 400b selects the child box associated with the patient's $BG_{TR}$, increments the $BG_{TR}$ count NTgr by one, and calculates the $BG_{TR}$ probability PTgr using Eq. 7.

At block 452, the training mode of the SubQ basal adjustment program 400b chronologically adjusts the basal insulin dose one dose adjustment at a time. The basal dose being adjusted is referred to as a Governing Basal dose (BasalGov). The program 400b may obtain the patient's BasalGov from the BG history data 208b and compare the patient's BasalGov to child boxes associated with the BasalGov attribute. Each child box may correspond to a BasalGov value or an associated range of BasalGov values. The program 400b selects the child box associated with the patient's BasalGov, increments a count NBasalG, and calculates a BasalGov probability PBasalG using Eq. 7. In some examples, the box associated with the patient's Basal- Gov is selected by iteratively comparing the patient's Basal-Gov to an upper bound of the BasalGov attribute (BasalG-Top) starting from the lowest BasalGov, and using a logic phrase in accordance with the following expression: IF BasalGov<BasalGTop THEN NBasalG=NBasalG+1.

At block 454, the training mode of the SubQ basal adjustment program 400b obtains the patient's next scheduled blood glucose measurement (BGgov) after the patient administers the BasalGov from the BG history data 208b and compares the BGgov to child boxes associated with the BGgov attribute. The BGgov associated with the patient's BasalGov occurs a sufficient amount of time after the patient administers the BasalGov when the dose is at a full activity level when the effects of food and rapid-acting insulin are both absent, and the blood glucose level is stable. Here, the program may flag the BGgov for identification. Each child box may correspond to a BGgov value or an associated range of BGgov values. The program 400a selects the child box associated with the patient's BGgov, increments a count NBG by one, and calculates the BGgov probability PBG using Eq. 7. In some examples, the box associated with the patient's BGgov is selected by iteratively comparing the patient's BGgov to an upper bound of the BGgov attribute (BGgovTop) starting from the lowest BGgov, and using a logic phrase in accordance with the following expression: IF BGgov<BGgov Top THEN NBG=NBG+1.

At block 456, the training mode of the SubQ basal adjustment program 400b obtains the patient's basal adjustment factor BAF from the SubQ information 208c and compares the patient's BAF to child boxes associated with the BAF attribute at block 456. Each child box may correspond to a BAF value or an associated range of BF values. The program 400b selects the child box associated with the patient's BAF, increments a count NBAF by one, and calculates the BAF probability PBAF using Eq. 7.

After the SubQ basal adjustment program 400b processes each of the patient's attributes within blocks 442-456, the program 400b proceeds to block 458 and obtains an Adjusted Basal dose (BasalAdj). The BasalAdj corresponds to the next scheduled basal dose occurring after the Basal-Gov of block 452. During the training mode, the program 400b compares the BasalAdj to child boxes associated with the BasalAdj attribute. Each child box may correspond to a BasalAdj value or an associated range of BasalAdj values. The program 400b selects the child box associated with the patient's BasalAdj, increments a count NBasalAdj by one, and calculates the BasalAdj probability PBasalAdj using Eq. 7. In some examples, the box associated with the patient's BasalAdj is selected by iteratively comparing the patient's BasalAdj to an upper bound of the BasalAdj attribute (BasalAdj Top) starting from the lowest BasalAdj, and using a logic phrase in accordance with the following expression: IF BasalAdj<BasalAdj Top THEN NBasalAdj=NBasalAdj+1. The SubQ basal adjustment program 400b may recommend an adjusted insulin dose associated with the BasalAdj to the patient 10 for the patient 10 to administer. For example, the dosing controller 160 may transmit the Basal-Adj to the patient computing device 110 or to the patient's administration device 123a, 123b.

Subsequent to processing the patient's BasalAdj at block 458, the SubQ basal adjustment program 400b, at block 460, obtains one or more outcome attributes associated with the patient's BasalAdj. The outcome attribute may include next scheduled breakfast BG measurement (BGbreakfastNext) occurring after the adjusted basal dose is administered by the patient at block 358. The program 400b may increment a count for the BGbreakfastNext (NBGbrkNext) by one.

Additionally, during the training mode, the program 400b may calculate an evaluation or a "grade" on the BasalAdj administered by the patient 10 based on the BGbreakfast-Next. For example, the program 400b may process the BGbreakfastNext to calculate the BGbreakfast Percent Error (BrkErr %) using Eq. 6 and increment a count for the BrkErr % (NBrkErr %) by one. The SubQ basal adjustment program 400b may also calculate a running sum for each BGbreak-fastNext (SumBGbrkNext) and each BrkErr % (SumBrkErr %) for each BasalAdj, and then average the BrkErr % (MeanBrkErr %) for each BasalAdj. The values for the SumBGbrkNext, the SumBrkErr %, and the MeanBrkErr % may be stored in a child box contained by a parent box corresponding to the BasalAdj. Accordingly, the basal adjustment program 400b calculates the evaluation or "grade" on each BasalAdj based on one or more outcome attributes associated with the BasalAdj. Here, BasalAdj values yielding favorable outcome attributes are assigned higher "grades" than those resulting in less favorable outcome attributes. Thus, the program 400b may identify a best or optimum treatment dose of insulin (e.g., best or optimum BasalAdj) from one of the BasalAdj doses of insulin administered by the patient 10 that yields the most favorable outcome attribute.

The training mode of the SubQ basal adjustment program 400b may proceed back to block 410 and obtain the BG history data 208b for another basal dose-adjustment history. Upon completing the training mode for each basal insulin dose to be adjusted, the SubQ basal adjustment program 400b stops the iterative process of incrementing the counts and calculating the probabilities within the non-transitory memory 24, 114, 124 at each of blocks 442-460. Thus, as with the training program 300a (FIG. 3A), the training mode of the SubQ basal adjustment program 400b builds a decision tree for a patient population based on the patient-state information 208a, BG history data 208b, and the SubQ information 208c for each patient of the patient population. Thereafter, the treatment mode of the SubQ basal adjustment program 400b may retrieve the decision tree from the non-transitory memory 24, 114, 124 to allow the user 40 (e.g., physical or medical professional) to prescribe an optimum BasalAdj that is personalized for a patient 10 being treated.

During the treatment mode, the SubQ basal adjustment program 400b uses the training data contained in the decision tree processed during the training mode for determining an optimum BasalAdj and recommending the optimum BasalAdj to a patient 10 in treatment. The treatment mode may commence at block 410 by obtaining patient-state information 208a, BG history data 208b, and SubQ information 208c associated with a new or returning patient 10 being treated. As with the training mode, the treatment mode of the SubQ basal adjustment program 400b may assign each of the new or returning patient's attributes into corresponding boxes at each of blocks 410-456. However, the treatment mode does not increment counts or calculate probabilities for the boxes associated with the patient's 10 attributes. At block 458, the program 400a selects the optimum insulin dose for the BasalAdj (e.g., optimum BasalAdj) for the new or returning patient 10 based on the BasalAdj from the training data of the training mode that is associated with a lowest MeanBrkErr %. Thus, the treatment mode of the program 400b selects the optimum BasalAdj that will yield a most favorable outcome attribute (e.g., lowest MeanBrkErr %) based on the training data of the training mode. Block 458 may use the reporting module 80 of the system 100 to recommend the optimum BasalAdj to the patient 10 being treated through transmission to the patient computing device 110 for the patient 10 to view upon the display, through transmission of an email containing the optimum BasalAdj, and/or printing the optimum BasalAdj in a report for the patient 10. In some examples, the dosing controller 160 executing the SubQ basal adjustment program 400b at block 458 may transmit the optimum BasalAdj to the administration device 123 (e.g., pump 123a or smart pen 123b) so that the administration computing device 112d, 112e may instruct the doser 223a, 223b to administer the optimum insulin dose to the patient 10.

Figure 4C:
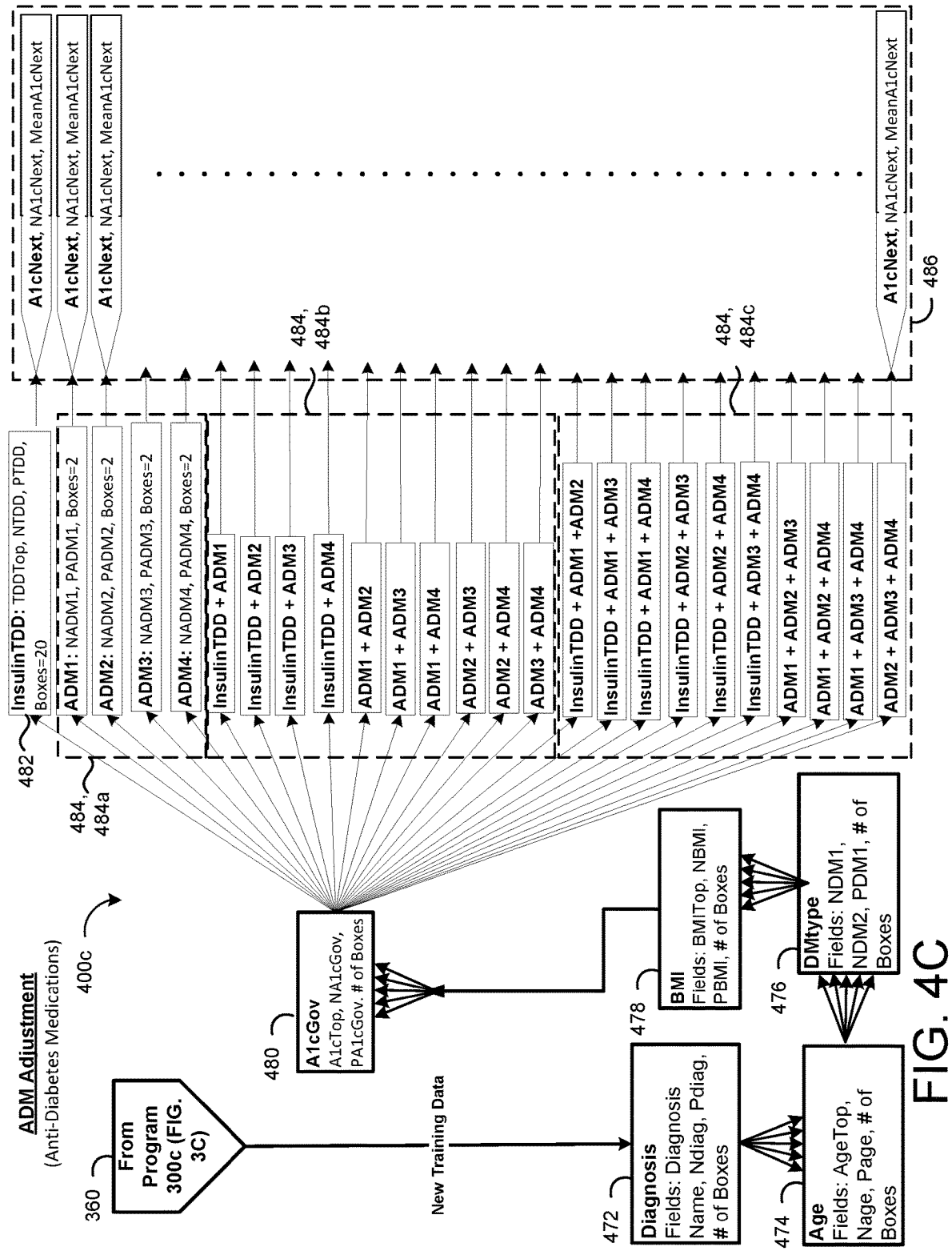
FIG. 4C is a schematic view of an anti-diabetes medication adjustment program.

Referring to FIG. 4C, in some implementations, the ADM adjustment program 400c may operate in training and treatment modes associated with the anti-diabetes program 300c (FIG. 3C). Accordingly, FIG. 4C provides details of the ADM adjustment process associated with the anti-diabetes program 300c (FIG. 3C). The ADM adjustment program 400c may use the new training data (e.g., patient-state information 208a and the BG history data 208b) from block 360 of the ADM program 300c of FIG. 3C which is sorted by patient ID and chronologically one ADM dose-combination adjustment at a time. Accordingly, the training mode of the ADM adjustment program 400c completes the process of obtaining the BG history data 208b associated with ADM dose-combination adjustments and outcome attributes associated therewith. Thus, each ADM dose-adjustment adjustment and the associated one or more outcome attributes may include a respective date-stamped event.

The ADM adjustment program 400c includes blocks 472-480 for processing associated attributes obtained from the new patient training data from block 322 that includes the patient's patient-state information 208a and the BG history data 208b. Each block 472-480 may obtain a count and calculate a probability for the associated attribute in the manner of tree-training based on the patient's patient-state information 208a and the BG history data 208b. Each block 472-480 may include one or more child attribute boxes associated with a parent attribute box. For each attribute, the blocks 472-480 may determine an appropriate box and increment the count (N) by one and calculate a likelihood or probability (P) in each box using Eq. 7.

The BG history data 208b may include a calculation of one or more ADM dose-combinations administered by the patient 10 and the outcome data corresponding to an A1c level associated with the one or more ADM dose-combinations administered by the patient 10. Additionally or alternatively, the outcome data may include a next scheduled blood glucose measurement BGnext occurring a sufficient time after the patient 10 administers the ADM dose-combination, and thereby showing the glycemic result of the ADM dose-combination. The ADM dose-combination refers to a dosing therapy that includes a combination of one or more non-insulin doses of anti-diabetes medications.

At blocks 472-480, the training mode of the ADM adjustment program 400c selects the child box, increments the count N by one and calculates the probability P within each box for each of the attributes associated with the patient's diagnosis, age, diabetic type DMtype, and body mass index (BMI) in the same manner as discussed above with reference to blocks 412-418 of the SubQ meal bolus adjustment program 400a (FIG. 4A) and blocks 442-448 of the SubQ basal adjustment program 400b (FIG. 4B).

At block 480, the training mode of the ADM adjustment program 400c chronologically adjusts the ADM dose-combination one dose adjustment at a time. The program uses the patient's A1c level (A1cGov) to govern the adjustment of the ADM dose-combination. The program 400c may obtain the patient's A1cGov from the BG history data 208b and compare the patient's A1cGov to child boxes associated with the A1cGov attribute. Each child box may correspond to an A1cGov value or an associated range of A1cGov values. The program 400c selects the child box associated with the patient's A1cGov, increments a count NA1cGov, and calculates a A1cGov probability PA1cGov using Eq. 7. In some examples, the box associated with the patient's A1cGov is selected by iteratively comparing the patient's BasalGov to an upper bound of the A1cGov attribute (A1cTop) starting from the lowest A1cGov, and using a logic phrase in accordance with the following expression: IF A1cGov<A1cTop THEN NA1cGov=NA1cGov+1. For example, block 480 may include child boxes corresponding to A1cTop values equal to 6.5, 7.5, 9.0, 10.0, 11.0, and 20.0.

At block 482, the patient's total daily dose (TDD) of insulin is sorted into boxes. While TDD is a SubQ parameter, the patient's TDD may be obtained from the patient-state information 208a using anyone of Eqs. 4A-4C. The program 400c may compare the patient's TDD to child boxes associated with the TDD attribute. Each child box may correspond to a TDD value or an associated range of TDD values. The program 400c selects the child box associated with the patient's TDD, increments a count NTDD, and calculates a TDD probability PTDD using Eq. 7. In some examples, the box associated with the patient's TDD is selected by iteratively comparing the patient's TDD to an upper bound of the TDD attribute (TDDTop) starting from the lowest TDD, and using a logic phrase in accordance with the following expression: IF TDD<TDDTop THEN NTDD=NTDD+1.

After the ADM adjustment program 400c processes each of the patient's attributes within blocks 472-482, the program 400c proceeds to one of blocks 484, 484a-c and obtains an adjusted ADM dose-combination. Many anti-diabetes medications (ADMs) currently exist and the number of available ADMs for treating patient's continues to increase. Moreover, some ADMs are withdrawn or fall out of favor for prescribing to patients when medical research discovers faults in those ADMs. Thus, the ADMs associated with the ADM dose-combinations of blocks 484a-c may be updated with new ADMs and/or with previously used ADMs being withdrawn. For simplicity, the ADM dose-combinations associated with blocks 484a-c may include four different ADMs (e.g., ADM1, ADM2, ADM3, ADM4) that may be used alone or in combination with one or more of the other ADMs.

At block 484a, the ADM adjustment program 400c obtains each of the patient's one or more ADMs from the patient-state information 208a and compare the patient's ADM(s) to child boxes associated with the ADM attribute. Each child box may correspond to a specific one of the ADMs. The program 400c selects each child box associated with the patient's one or more ADMs, increments a count NADM1-4 for each box selected, and calculates ADM probability PADM1-4 for each box selected using Eq. 7.

The ADM dose-combinations of block 484a are each associated with a mono-therapy including an adjusted ADM dose of only one of ADM1, ADM2, ADM3, or ADM4. The ADM dose-combinations of block 484b are associated with a dual-therapy including an adjusted ADM dose-combination of any two of the ADMs 1-4. The ADM dose-combinations of block 484c are associated with a triple-therapy including an adjusted ADM dose-combination of any three of the ADMs 1-4. Therapies including ADM dose-combinations of four or more ADM may exist when more than five ADMs are available for treating patients for delaying, and in some instances, eliminating the progression of diabetes in patients. The training mode of the ADM adjustment program 400c may also increment counts and calculated probabilities for each of the dose-combinations of block 484b associated with the dual-therapy and each of the dose-combinations of block 484c associated with the triple-therapy.

At block 486, the ADM adjustment program 400c obtains one or more outcome attributes associated with each of the adjusted ADM dose-combinations of blocks 484a-484c. In some examples, an outcome attribute associated with the ADM dose-combinations may include a next A1c result (A1cNext) occurring after the associated adjusted ADM dose-combination is administered by the patient 10. Block 486 may obtain the patient's A1cNext from the BG History data 208b and compare the patient's A1cNext to child boxes associated with the A1cNext attribute. The program 400c selects the child box associated with the patient's A1cNext and increments a count NA1cNext for the selected box by one.

The training mode of the ADM adjustment program 400c may proceed back to block 322 and obtain the BG history data 208b for another ADM dose-adjustment history. Upon completing the training mode for each ADM dose-combination to be adjusted, the ADM adjustment program 400c stops the iterative process of incrementing the counts and calculating the probabilities within the non-transitory memory 24, 114, 124. Thus, the ADM adjustment program 400c builds a decision tree for a patient population based on the patient-state information 208a and the BG history data 208b for each patient of the patient population. In some implementations, block 486 averages all of the obtained A1cNext values (MeanA1CNext) for each of the ADM dose-combinations administered by patients of the patient population. Thereafter, the treatment mode of the ADM adjustment program 400c may retrieve the decision tree from the non-transitory memory 24, 114, 124 to allow the user 40 (e.g., physical or medical professional) to prescribe an optimum ADM dose-combination that is personalized for a patient 10 being treated. For example, the treatment mode of the ADM adjustment program 400c may select an optimum ADM dose-combination from one of blocks 484a-484c for a new or returning patient that corresponds to the ADM dose-combination associated with the lowest MeanA1cNext obtained from the training data of the training mode at block 486.

Figure 5:
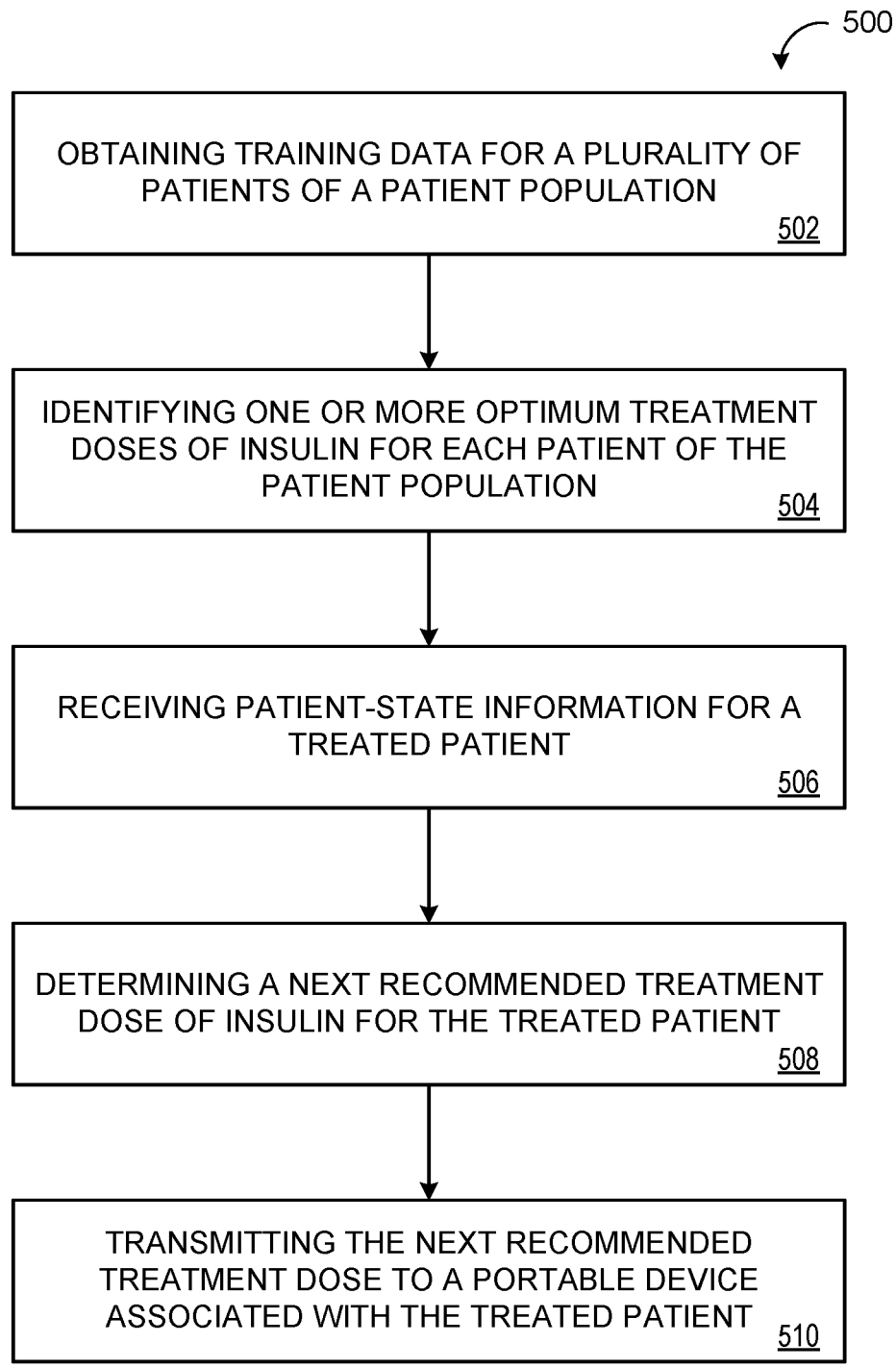
FIG. 5 is an exemplary arrangement of operations for determining a treatment dose for a treated patient.

Referring to FIG. 5, a method 500 of determining a treatment dose of insulin for a treated patient 10 includes obtaining 502 training data 310 for a plurality of patients 10 of a patient population at data processing hardware 112, 132, 142, 192 from memory hardware 24, 114, 134, 144, 194 in communication with the data processing hardware 112, 132, 142, 192. The training data 310 includes training blood glucose history data 208b and training patient-state information 208a for each patient 10 of the patient population. The training blood glucose history data 208b includes treatment doses 316, 336 of insulin administered by the patients 10 of the patient population and one or more outcome attributes 318, 338 associated with each treatment dose 316 of insulin. The method 500 includes the data processing hardware 112, 132, 142, 192 identifying 504, for each patient 10 of the patient population, one or more optimum treatment doses 340 of insulin from the treatment doses 316, 336 of insulin yielding favorable outcome attributes 318, 338.

The method 500 also includes receiving 506 patient-state information 208a for the treated patient 10 at the data processing hardware 112, 132, 142, 192 and the data processing hardware 112, 132, 142, 192 determining 508 a next recommended treatment dose of insulin for the treated patient 10 based on one or more of the identified optimum treatment doses 340 associated with patients 10 of the patient population having training patient-state information 310, 208a similar to the patient-state information 208a for the treated patient 10. The method 500 includes transmitting 510 the next recommended treatment dose to a portable device 110, 123, 124 associated with the treated patient. The portable device 110, 123, 124 may display the next recommended treatment dose.

Various implementations of the systems and techniques described here can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Moreover, subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The terms "data processing apparatus", "computing device" and "computing processor" encompass all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as an application, program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

One or more aspects of the disclosure can be implemented in a computing system that includes a backend component, e.g., as a data server, or that includes a middleware component, e.g., an application server, or that includes a frontend component, e.g., a client computer having a graphical user interface or a Web browser through which a user can interact with an implementation of the subject matter described in this specification, or any combination of one or more such backend, middleware, or frontend components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specifics, these should not be construed as limitations on the scope of the disclosure or of what may be claimed, but rather as descriptions of features specific to particular implementations of the disclosure. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A computer-implemented method executed on data processing hardware that causes the data processing hardware to perform operations comprising:
   obtaining training data for a plurality of patients of a patient population from memory hardware in communication with the data processing hardware, the training data comprising, for each particular patient of the patient population:
      one or more ADM dose-combinations administered to the particular patient;
      a corresponding outcome attribute associated with each of the one or more ADM dose-combinations administered to the particular patient; and
      corresponding training patient-state information;
   processing the training data for each of the plurality of patients of the patient population to train a predictive model capable of predicting ADM dose-combinations for a patient being treated;
   for each particular patient of the patient population, identifying, using the trained predictive model, a corresponding optimum ADM dose-combination that yields a corresponding outcome attribute associated with bringing and maintaining a corresponding glucose level of the particular patient closest to a glucose target center of a glucose target range;
   receiving patient-state information for the patient being treated;
   identifying a subset of the patients of the patient population having corresponding training patient-state information similar to the received patient-state information for the patient being treated;
   determining a recommended ADM dose-combination for the patient being treated based on the corresponding optimum ADM dose-combinations identified for the identified subset of the patients, the ADM dose-combination comprising a particular dosage of a particular ADM; and
   transmitting instructions to an administration device associated with the patient to administer the recommended ADM dose-combination to the patient being treated, the instructions, when received by the administration device, causing the administration device to administer the recommended ADM dose-combination to the patient being treated.

2. The method of claim 1, wherein obtaining the training data comprises obtaining the training data periodically at an end of a re-occurring configurable time interval.

3. The method of claim 1, wherein obtaining the training data comprises obtaining the training data immediately in response to a user input selecting an immediate start button displayed upon a display in communication with the data processing hardware.

4. The method of claim 1, wherein obtaining the training data comprises obtaining the training data on a selected date.

5. The method of claim 1, wherein the corresponding outcome attributes associated with the one or more ADM dose-combinations administered to the particular patient comprises a glycated hemoglobin measurement associated with the one or more ADM dose-combinations administered to the particular patient.

6. The method of claim 5, wherein the operations further comprise:
   receiving a glycated hemoglobin measurement for the patient being treated,
   wherein determining the recommended ADM dose-combination for the patient being treated is further based on the glycated hemoglobin measurement for the patient being treated.

7. The method of claim 1, wherein the recommended ADM dose-combination comprises a non-insulin dose-combination.

8. The method of claim 1, wherein the recommended ADM dose-combination comprises a dual- or triple-therapy including insulin and at least one non-insulin ADM.

9. The method of claim 1, wherein at least one of the ADM dose-combinations for at least one corresponding patient of the patient population comprises a dual-therapy including an ADM dose-combination comprising two ADMs.

10. The method of claim 1, wherein at least one of the ADM dose-combinations for at least one corresponding patient of the patient population comprises a triple-therapy including a ADM dose-combination comprising two ADMs.

11. The method of claim 1, wherein the patient being treated is diagnosed with Type 2 diabetes mellitus.

12. The method of claim 1, wherein the patient-state information for a patient comprises a plurality of patient-state attributes associated with the patient, the patient-state attributes including one or more of an age, a gender, a medical history, a body mass index, a medical history, risk factors, and/or financial attributes.

13. A system comprising:
   a dosing controller including data processing hardware and memory hardware in communication with the data processing hardware, the memory hardware storing instructions that, when executed by the data processing hardware, cause the dosing controller to perform operations comprising:
      obtaining training data for a plurality of patients of a patient population from memory hardware in communication with the data processing hardware, the training data comprising, for each particular patient of the patient population:
         one or more ADM dose-combinations administered to the particular patient;
         a corresponding outcome attribute associated with each of the one or more ADM dose-combinations administered to the particular patient; and
         corresponding training patient-state information;
      processing the training data for each of the plurality of patients of the patient population to train a predictive model capable of predicting ADM dose-combinations for a patient being treated;
      for each particular patient of the patient population, identifying, using the trained predictive model, a corresponding optimum ADM dose-combination that yields a corresponding outcome attribute associated with bringing and maintaining a corresponding glucose level of the particular patient closest to a glucose target center of a glucose target range;
      receiving patient-state information for the patient being treated;
      identifying a subset of the patients of the patient population having corresponding training patient-state information similar to the received patient-state information for the patient being treated;
      determining a recommended ADM dose-combination for the patient being treated based on the corresponding optimum ADM dose-combinations identified for the identified subset of the patients, the ADM dose-combination comprising a particular dosage of a particular ADM; and transmitting instructions to an administration device associated with the patient to administer the recommended ADM dose-combination to the patient being treated, the instructions, when received by the administration device, causing the administration device to administer the recommended ADM dose-combination to the patient being treated.

14. The system of claim 13, wherein obtaining the training data comprises obtaining the training data periodically at an end of a re-occurring configurable time interval.

15. The system of claim 13, wherein obtaining the training data comprises obtaining the training data immediately in response to a user input selecting an immediate start button displayed upon a display in communication with the data processing hardware.

16. The system of claim 13, wherein obtaining the training data comprises obtaining the training data on a selected date.

17. The system of claim 13, wherein the corresponding outcome attributes associated with the one or more ADM dose-combinations administered to the particular patient comprises a glycated hemoglobin measurement associated with the one or more ADM dose-combinations administered to the particular patient.

18. The system of claim 17, wherein the operations further comprise:

receiving a glycated hemoglobin measurement for the patient being treated, wherein determining the recommended ADM dose-combination for the patient being treated is further based on the glycated hemoglobin measurement for the patient being treated.

19. The system of claim 13, wherein the recommended ADM dose-combination comprises a non-insulin dose-combination.

20. The system of claim 13, wherein the recommended ADM dose-combination comprises a dual- or triple-therapy including insulin and at least one non-insulin ADM.

21. The system of claim 13, wherein at least one of the ADM dose-combinations for at least one corresponding patient of the patient population comprises a dual-therapy including an ADM dose-combination comprising two ADMs.

22. The system of claim 13, wherein at least one of the ADM dose-combinations for at least one corresponding patient of the patient population comprises a triple-therapy including a ADM dose-combination comprising two ADMs.

23. The system of claim 13, wherein the patient being treated is diagnosed with Type 2 diabetes mellitus.

24. The system of claim 13, wherein the patient-state information for a patient comprises a plurality of patient-state attributes associated with the patient, the patient-state attributes including one or more of an age, a gender, a medical history, a body mass index, a medical history, risk factors, and/or financial attributes.

* * * * *